US006465254B1

(12) United States Patent
Saito et al.

(10) Patent No.: US 6,465,254 B1
(45) Date of Patent: Oct. 15, 2002

(54) MUTANT LOXP SITE AND APPLICATIONS THEREOF

(75) Inventors: Izumu Saito, Tokyo; Keiji Tanaka, Kyoto, both of (JP)

(73) Assignee: Sumitomo Pharmaceuticals Company, Limited, Osaka (JP)

( * ) Notice: Subject to any disclaimer, the term of this patent is extended or adjusted under 35 U.S.C. 154(b) by 0 days.

(21) Appl. No.: 09/554,271

(22) PCT Filed: Nov. 12, 1998

(86) PCT No.: PCT/JP98/05094

§ 371 (c)(1),
(2), (4) Date: Jul. 7, 2000

(87) PCT Pub. No.: WO99/25851

PCT Pub. Date: May 27, 1999

(30) Foreign Application Priority Data

Nov. 13, 1997 (JP) .............................................. 9-331289
Sep. 28, 1998 (JP) ............................................ 10-273150

(51) Int. Cl.[7] ........................ C12N 15/87; C07H 21/04; A01N 65/00
(52) U.S. Cl. ...................... 435/462; 435/463; 435/455; 536/23.1; 424/93.1
(58) Field of Search ................................. 435/455, 462, 435/463; 800/21; 424/93.21; 536/231

(56) References Cited

U.S. PATENT DOCUMENTS 6,228,646 B1 * 5/2001 Hardy ......................... 435/455
6,271,436 B1 * 8/2001 Piedrathita et al. ............ 800/21

OTHER PUBLICATIONS

Sauer; Multiplex Cre//ox recombiantjon permits selective site–specific DNA targeting to both a natural and an engineered site in the yeast genome, 1996, Nucleic Acids Research vol. 24, No. 23: 4608–4613.*

Verma et al.; Gene Therapy–promises, problems and prospects, 1997, Nature vol. 389:239–242.*
Eck et al.; Gene–Based Therapy, 1995, Pharmacological Basis of Therapeutics : 77–101.*
Gwang Lee et al., "Role of nucleotide sequences of loxP spacer region in Cre–mediated recombination", *Gene* (1998) vol. 216, No. 1 p. 55–65.
Y. Sakai et al., "Highly enhanced and specific expression for hepatocellular carcinoma in vivo using recombinant adenovirus vector with cre/loxP system", *Hepatology* (1997) vol. 26, No. 4, Pt. 2 p. 171A.

(List continued on next page.)

*Primary Examiner*—James Ketter
*Assistant Examiner*—Janice Li
(74) *Attorney, Agent, or Firm*—Sughrue Mion, PLLC

(57) ABSTRACT

Highly efficient gene integration or gene replacement in the higher eucaryote including animal cells can be performed by using mutant loxP site having the following properties (a)–(c) in the present invention.

(a) a nucleotide sequence wherein, in a wild-type loxP site of the following formula (SEQ ID NO: 1) derived from *E. coli* P1 phage, at least one of the bases consisting of second (T), third (G), fourth (T) and fifth (A) bases, and at least one of the bases consisting of sixth (T) and seventh (G) bases within the 8 bases in the central part of the sequence (spacer region) are substituted by different base, and regions except for the spacer region are optionally substituted by any base:

```
                    12345678
5'-ATAACTTCGTATA ATGTATGC TATACGAAGTTAT-3'
                  Spacer Region
```

(b) a specific recombination between said mutant loxP and the wild-type loxP site can not occur even in the presence of recombinase Cre; and
(c) a specific recombination between the mutant loxP sites having identical nucleotide sequences can occur in the presence of recombinase Cre.

34 Claims, 16 Drawing Sheets

OTHER PUBLICATIONS

Ronald H. Hoess et al., "The role of the loxP spacer region in P1 site–specific recombination", *Nucleic Acid Research* (1986) vol. 14, No. 5, p. 2287–2300.

International Search Research.

Naoya Tsurushita, et al., "Phage Display Vectors For in Vivo Recombination of Immunoglobulin Heavy and Light Chain Genes to Make Large Combinatorial Libraries" Gene, 1996, vol. 172, 59–63.

Peter Waterhouse, et al. "Combinatorial Infection and in vivo Recombination: A Strategy for Making Large Phage Antibody Repertoires" Nucleic Acids Research, 1993, vol. 21, No. 9, 2265–2266.

Bruce Bethke, et al. "Segmental Genomic Replacement by Cre–Mediated Recombination: Genotixic Stress Activation of The p53 Promoter In Single–Copy Transformants" Nucleic Acids Research 1997, vol. 25, No. 14, 2828–2834.

* cited by examiner

FIG. 2

Single-Base Substitution
(Sense)

```
            12345678
wilds  5' - ATGTATGC -3'
 11s   5' - GTGTATGC -3'
 12s   5' - TTGTATGC -3'
 13s   5' - CTGTATGC -3'
 21s   5' - ACGTATGC -3'
 22s   5' - AAGTATGC -3'
 23s   5' - AGGTATGC -3'
 31s   5' - ATATATGC -3'
 32s   5' - ATCTATGC -3'
 33s   5' - ATTTATGC -3'
 41s   5' - ATGCATGC -3'
 42s   5' - ATGAATGC -3'
 43s   5' - ATGGATGC -3'
 51s   5' - ATGTGTGC -3'
 52s   5' - ATGTTTGC -3'
 53s   5' - ATGTCTGC -3'
 61s   5' - ATGTACGC -3'
 62s   5' - ATGTAAGC -3'
 63s   5' - ATGTAGGC -3'
 71s   5' - ATGTATAC -3'
 72s   5' - ATGTATCC -3'
 73s   5' - ATGTATTC -3'
 81s   5' - ATGTATGT -3'
 82s   5' - ATGTATGG -3'
 83s   5' - ATGTATGA -3'
```

FIG. 3

Single-Base Substitution
(Antisense)

```
            87654321
wilda  5' - GCATACAT -3'
 11a   5' - GCATACAC -3'
 12a   5' - GCATACAA -3'
 13a   5' - GCATACAG -3'
 21a   5' - GCATACGT -3'
 22a   5' - GCATACTT -3'
 23a   5' - GCATACCT -3'
 31a   5' - GCATATAT -3'
 32a   5' - GCATAGAT -3'
 33a   5' - GCATAAAT -3'
 41a   5' - GCATGCAT -3'
 42a   5' - GCATTCAT -3'
 43a   5' - GCATCCAT -3'
 51a   5' - GCACACAT -3'
 52a   5' - GCAAACAT -3'
 53a   5' - GCAGACAT -3'
 61a   5' - GCGTACAT -3'
 62a   5' - GCTTACAT -3'
 63a   5' - GCCTACAT -3'
 71a   5' - GTATACAT -3'
 72a   5' - GGATACAT -3'
 73a   5' - GAATACAT -3'
 81a   5' - ACATACAT -3'
 82a   5' - CCATACAT -3'
 83a   5' - TCATACAT -3'
```

FIG. 4
Double-Base Substitutions (Sense)

```
          12345678
wilds  5'- ATGTATGC -3'
2171s  5'- ACGTATAC -3'
2172s  5'- ACGTATCC -3'
2173s  5'- ACGTATTC -3'
2271s  5'- AAGTATAC -3'
2272s  5'- AAGTATCC -3'
2273s  5'- AAGTATTC -3'
2371s  5'- AGGTATAC -3'
2372s  5'- AGGTATCC -3'
2373s  5'- AGGTATTC -3'
3171s  5'- ATATATAC -3'
3172s  5'- ATATATCC -3'
3271s  5'- ATCTATAC -3'
3272s  5'- ATCTATCC -3'
3371s  5'- ATTTATAC -3'
3372s  5'- ATTTATCC -3'
3373s  5'- ATTTATTC -3'
4171s  5'- ATGCATAC -3'
4172s  5'- ATGCATCC -3'
4271s  5'- ATGAATAC -3'
4272s  5'- ATGAATCC -3'
4371s  5'- ATGGATAC -3'
4372s  5'- ATGGATCC -3'
4373s  5'- ATGGATTC -3'
5171s  5'- ATGTGTAC -3'
5272s  5'- ATGTTTCC -3'
5373s  5'- ATGTCTTC -3'
6171s  5'- ATGTACAC -3'
6272s  5'- ATGTAACC -3'
6373s  5'- ATGTAGTC -3'
```

FIG. 5
Double-Base Substitutions (Antisense)

```
          87654321
wilda  5'- GCATACAT -3'
2171a  5'- GTATACGT -3'
2172a  5'- GGATACGT -3'
2173a  5'- GAATACGT -3'
2271a  5'- GTATACTT -3'
2272a  5'- GGATACTT -3'
2273a  5'- GAATACTT -3'
2371a  5'- GTATACCT -3'
2372a  5'- GGATACCT -3'
2373a  5'- GAATACCT -3'
3171a  5'- GTATATAT -3'
3172a  5'- GGATATAT -3'
3271a  5'- GTATAGAT -3'
3272a  5'- GGATAGAT -3'
3371a  5'- GTATAAAT -3'
3372a  5'- GGATAAAT -3'
3373a  5'- GAATAAAT -3'
4171a  5'- GTATGCAT -3'
4172a  5'- GGATGCAT -3'
4271a  5'- GTATTCAT -3'
4272a  5'- GGATTCAT -3'
4371a  5'- GTATCCAT -3'
4372a  5'- GGATCCAT -3'
4373a  5'- GAATCCAT -3'
5171a  5'- GTACACAT -3'
5272a  5'- GGAAACAT -3'
5373a  5'- GAAGACAT -3'
6171a  5'- GTGTACAT -3'
6272a  5'- GGTTACAT -3'
6373a  5'- GACTACAT -3'
```

FIG. 6
Arrows show BsaHI sites
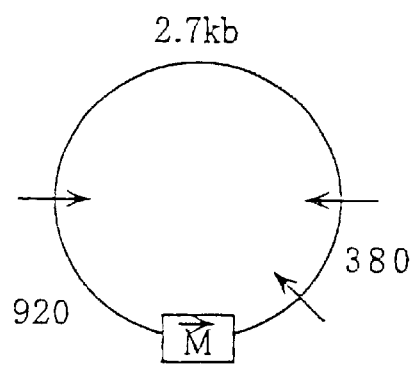
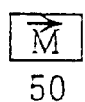
50

FIG. 14
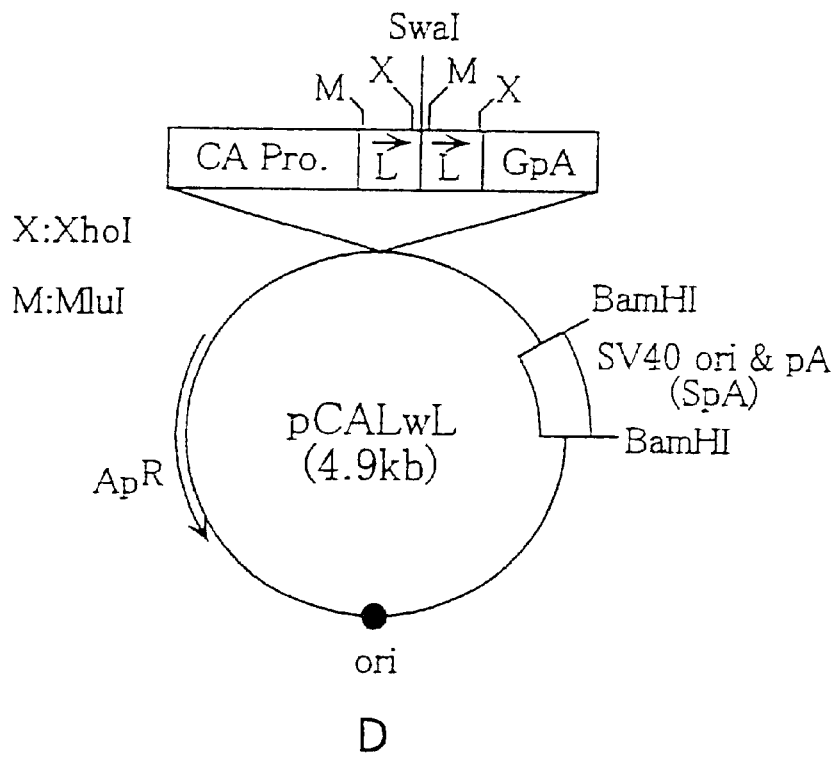
D
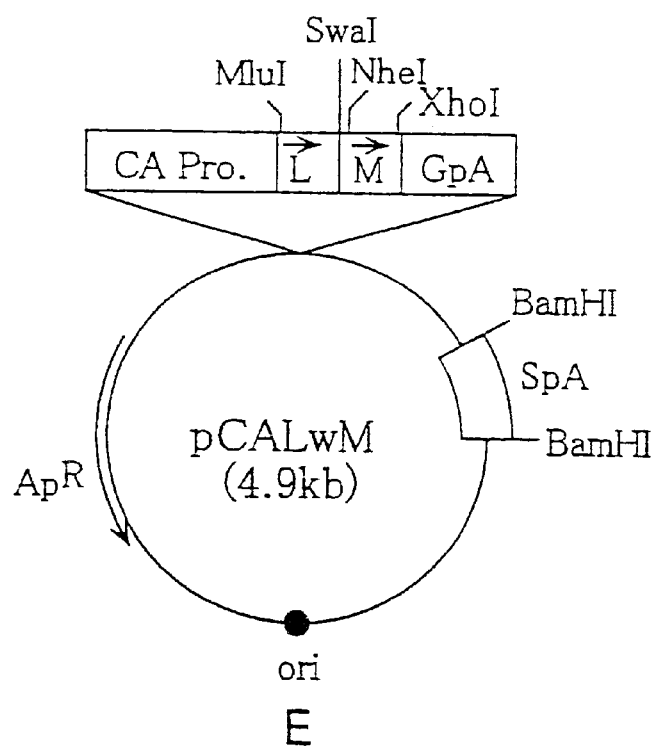
E

FIG. 15
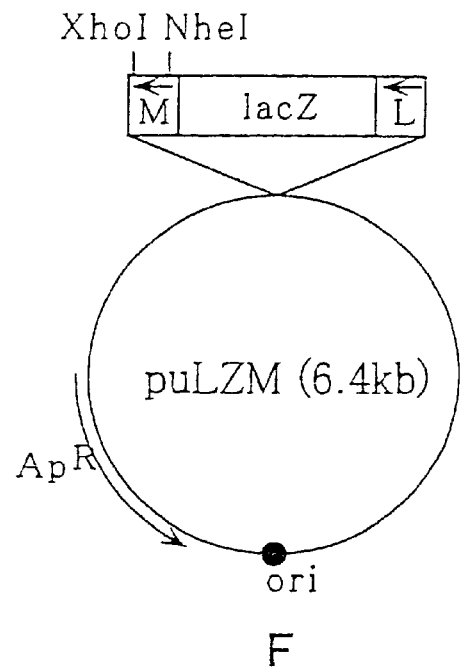
F
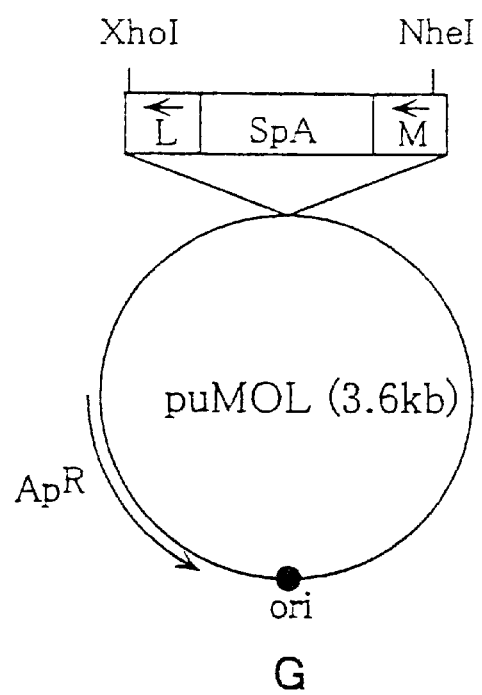
G

FIG. 16
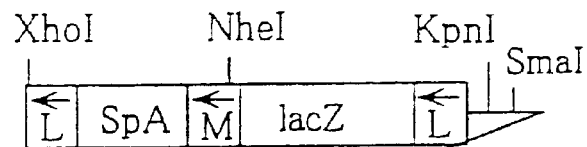
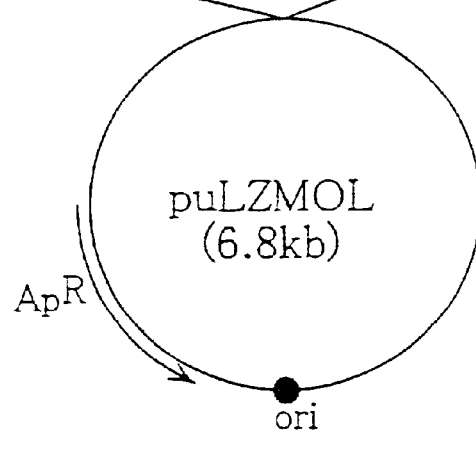
H
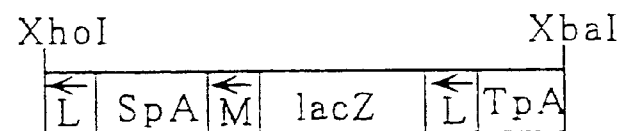
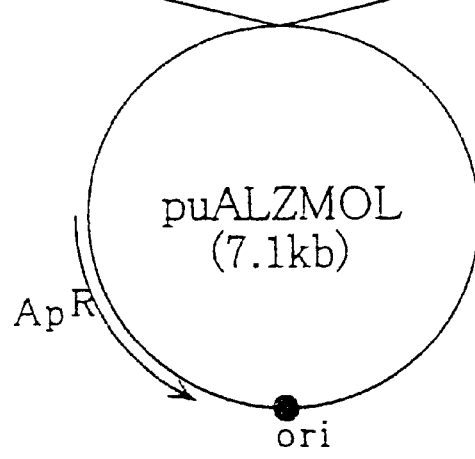
I

MUTANT LOXP SITE AND APPLICATIONS THEREOF

TECHNICAL FIELD

This invention relates to a mutant loxP site and applications thereof. More particularly, the present invention relates to the mutant loxP site, in which a specific recombination between the mutant loxP site and a wild-type loxP site can not occur, but a specific recombination between mutant loxP sites can occur in each other, and gene replacement using the said mutant loxP site.

BACKGROUND ART

It is not so easy to integrate any gene into specific sites of animal virus or chromosome of animal cells of the higher eucaryotes or to delete specific gene therefrom. A conventional method for gene integration into the specific site of chromosome of animal cells is, for example, that cells are transformed with plasmid DNA, to which DNA having the same site with the site of chromosome to be intended to integrate is ligated with both sites of the objective gene, to obtain the cells, to which the objective gene is integrated by homologous recombination. Frequency of homologous recombination is, however, extremely low. To that end, the objective gene and drug resistant gene should be simultaneously integrated and selected by drug. Consequently, several months have to be required to obtain the objective cells. Further, although preparation of recombinant animal virus, to which the objective gene is integrated, is slightly easier than the previously described case of chromosome of cells, however even in case that, for example, the recombinant adneovirus is constructed, various treatments including homologous recombination by using plasmids, to which objective gene is integrated, as well as cloning, selection and growth of the recombinant virus are required (Bett et al., Proc. Natl. Acad. Sci., 91: 8802–8806, 1999 and Miyake et al., ibid. 93: 1320–1324, 1996).

One of reasons why the gene manipulation of specific sites in chromosome of animal cells and the construction of recombinant virus are difficult is using homologous recombination with low frequency. Contrary to that, if it can be used enzymes, which can specifically recognize DNA Sequence, as like restriction enzymes used for construction of plasmid or bacteriophage, it is expected to improve the efficiency of the gene manipulation on cell chromosome. Example of such the enzyme is recombinase Cre derived from bacteriophage P1 of *E. coli*.

Cre is a specific DNA recombinase, which recognizes specific nucleotide sequence (loxP site) and conducts total processes including DNA strand cleavage, strand exchange and ligation of each DNA strand within this site (Sternberg et al., J. Mol. Biol., 150: 467–468, 1981; Abremski et al., J. Biol. Chem., 259: 1509–1514, 1984; and Hoess et al., Proc. Natl. Acad. Sci., 81: 1026–1029, 1984). In case that two loxP sites of the same direction exist within the same DNA molecule, DNA sequence between them is excised to form circular molecule (DNA excision reaction), or on the contrary in case that two loxP sites exist in the different DNA molecules, and the one is a circular DNA, the circular DNA is inserted into the other DNA molecule through loxP site (insertion reaction). Although Cre and loxP site were found in bacteriophage, the specific DNA recombination reaction is known to function not only in the procaryotes but also in the eucaryotes including animal cells and in the animal viruses. Examples of excision reactions are cultured animal cells (Sauer et al., Nucleic Acids Res., 17: 147–161, 1989 and Kanegae et al., Gene, 181: 207–212, 1996), animal viruses (Sauer et al., Proc. Natl. Acad. Sci., 85: 5166–5170, 1988; Anton et al., J. Virol., 69: 4600–4606, 1995; and Kanegae et al., Nucleic Acids Res., 23: 3816–3821, 1995), and transgenic mice (Lakso et al., Proc. Natl. Acad. Sci., 89: 6232–6236, 1992; Orban et al., ibid., 89: 6861–6865, 1992; Gu et al., Cell, 73: 1155–1164, 1993 and Gu et al., Science, 265: 103–106, 1994).

In addition, if the insertion reaction is applied, any gene can be inserted into the chromosome of animal cells or viral genome, in which loxP site exists previously, but the frequency of insertion is extremely low (Fukushige et al., Proc. Natl. Acad. Sci., 89: 7905–79029, 1992 and Sauer et al., Proc. Natl. Acad. Sci., 84: 9108–9112, 1987), consequently it is not practicable. Because, the insertion and excision are irreversible reactions, consequently if two loxP sites are existed in the identical DNA molecule as a result of insertion reaction, the excision reaction immediately occurs, moreover a reaction equilibrium lies overwhelmingly so far to the excision reaction.

In order to increase frequency of the insertion reaction, trials on using loxP site (mutant type), which is different from the original nucleotide sequence of loxP site (wild-type), were performed. The loxP site consists of DNA sequence of 34 bp (SEQ ID NO: 1), as shown below in both the 5' to 3' and the 3' to 5' direction. Among them, 8 bp sequence between two 13 bp inverted repeats is designated as spacer region, and recombination of DNA strand is known to be carried out within the spacer region (Hoess et al., J. Mol. Biol., 181: 351–362, 1985).

```
              loxP site (34bp)
         <------------------------>
                    12345678
  5'-ATAACTTCGTATA ATGTATGC TATACGAAGTTAT-3'
  3'-TATTGAAGCATAT TACATACG ATATGCTTCAATA-5'
     Inverted       Spacer      Inverted
     Repeat         Region      Repeat
      (13bp)         (8bp)       (13bp)
```

It was shown that the specific DNA recombination reaction between loxP site (mutant loxP site), in which a base at position 7 in the spacer region is substituted from G (guanine) to A (adenine), and wild-type loxP sequence can not occur, but the specific DNA recombination reaction between two mutant loxP sites can occur (Hoess et al., Nucleic Acids Res., 14: 2287–2300, 1986).

Trials that a gene located between mutant loxP site and wild-type loxP site in the DNA molecule is inserted between mutant loxP site and wild-type loxP site in the other DNA molecule or replaced by the other gene between them, are carried out. Examples of these trials are replacement of a gene on the plasmid vector by a gene on the bacteriophage gene (Waterhouse et al., Nucleic Acids Res., 21: 2265–2266, 1993), insertion of a gene on the phagemid vector to the plasmid vector (Tsurushita et al., Gene, 172: 59–63, 1996) and replacement of a gene on the plasmid vector by a gene on the chromosome of animal cells (Bethke et al., Nucleic Acids Res., 25: 2828–2834, 1997).

These trials were, however, performed by using only one mutant loxP site, i.e. the loxP site in which a base at position 7 of the spacer region was substituted from G (guanine) to A (adenine) (mutant loxP site), and the fact that whether it is preferable or not, is unknown, because the recombination reaction between the mutant loxP site in the said sequence and the wild-type loxP site does not occur. Further, in the above all three trials, the experimental systems, in which the drug resistant gene itself or the drug resistant gene together with objective gene is inserted and as a result, the recombinants having DNA molecules accompanied with the objective recombination can only acquire drug resistance and amplyfy, are used. Consequently, even if efficiency of the actual gene insertion (gene replacement) is low due to the recombiantion between the loxP site with incomplete mutation and the wild-type loxP site, such the experimental result is biased by the selection with drug resistance, and the apparent reaction efficiency may possibly be expressed too high.

Actually, as a result of direct and quantitative measurement found by us, in the mutant loxP site with substitution from G to A at position 7, a recombination reaction between it and the wild-type loxP sequence occurs with frequency of approximately 5%, which shows incomplete mutation of the loxP site.

As explained hereinabove, in the prior art, a technique for performing gene replacement in the chromosome in animal cells using mutant loxP site and wilt-type loxP site has tried, but its efficiency was not sufficient.

DISCLOSURE OF INVENTION

An object of the present invention is to provide a mutant loxP site wherein, in the presence of recombinase Cre, recombination with a wild-type loxP site can not occur, and recombination between two mutant loxP sites having the identical sequence can occur at the almost same efficiency of the recombination between two wild-type loxP sites. Further object of the present invention is to provide a method for gene integration or gene replacement with high efficiency in higher eukaryote including animal cells by the combination of the wild-type loxP site and the mutant loxP site, or the combination of the mutant loxP sites having different sequences in each other. More further object of the present invention is to provide application of such the methods for gene transfer to animal and plant cells, construction of recombinant viruses, gene manipulation in the animal and plant bodies, and the like.

We have studied a mechanism of recombinase Cre-dependent recombination between two loxP sites and identified nucleotide sequence of loxP site essential for the reaction, as a result of preparing mutant loxP sites with possible single base substitution for all of 8 bases in the spacer region of loxP site and studying the reactivity by means of very sensitive assay method. Accordingly, we have identified, on the basis of these findings, the mutant loxP site, in which a recombination between two mutant loxP sites having the identical sequence can occur with nearly equal efficiency of the recombination between two wild-type loxP sites, and a recombination between the mutant loxP site and the wild-type loxP site or between the mutant loxP sites having different sequence can not occur. Further we have succeeded, as a result of combining these loxP sites, to integrate a gene with extremely high efficiency into chromosome of animal cells. The present invention has been completed based on these findings and as a result of further progress of studies.

Accordingly, the gist of the present invention is as shown in the following (1)–(2 1);

(1) A mutant loxP site having following properties:
  (a) a nucleotide sequence wherein, in a wild-type loxP site of the following formula (SEQ ID NO: 1) derived from *E. coli* P1 phage, at least one of the bases consisting of second (T), third (G), fourth (T) and fifth (A) bases, and at least one of the bases consisting of sixth (T) and seventh (G) bases within the 8 bases in the central part of the sequence (spacer region) are substituted by different bases, and regions except for the spacer Region are optionally substituted by any base;

```
                 12345678
5'-ATAACTTCGTATA ATGTATGC TATACGAAGTTAT-3'
                Spacer Region
```

(b) a specific recombination between said mutant loxP site and the wild-type loxP site can not occur even in the presence of recombinase Cre; and
  (c) a specific recombination between the mutant loxP sites having identical nucleotide sequences can occur in the presence of recombinase Cre.

(2) A mutant loxP site having following properties:
  (a) a nucleotide sequence wherein, in a wild-type loxP site of the following formula (SEQ ID NO: 1) derived from *E. coli* P1 phage, a base selected from the group consisting of second (T), third (G) and fourth (T) bases is substituted by a different base, and regions except for the spacer region are optionally substituted by any base;

```
                 12345678
5'-ATAACTTCGTATA ATGTATGC TATACGAAGTTAT-3'
                Spacer Region
```

(b) a specific recombination between the said mutant loxP site and the wild-type loxP site can not occur even in the presence of recombinase Cre; and
  (c) a specific recombination between the mutant loxP site having identical nucleotide sequences can occur in the presence of recombinase Cre.

(3) The mutant loxP site according to (1) or (2) above, wherein the specific DNA recombination between the mutant loxP site and another mutant loxP site having different nucleotide sequence can not occur in the presence of recombinase Cre.

(4) The mutant loxP site according to (1) above, wherein the nucleotide sequence is expressed by SEQ ID NO: 26, SEQ ID NO: 29, SEQ ID NO: 30, SEQ ID NO: 35, SEQ ID NO: 39, SEQ ID NO: 42, or SEQ ID NO: 49.

(5) A DNA comprising the mutant loxP site according to any one of (1) to (4) above.

(6) A DNA comprising at least one wild-type loxP site and at least one mutant loxP site according to (1) or (2) above.

(7) The DNA according to (6) above wherein a desired gene is inserted between the wild-type loxP site and the mutant loxP site.

(8) A DNA comprising at least two mutant loxP sites having different nucleotide sequence in each other according to (3) above.

(9) The DNA according to (8) above wherein a desired gene is inserted between two mutant loxP sites having different nucleotide sequence in each other.

(10) A cell which is transformed by DNA according to any one of (6) to (9) above.

(11) A method for replacing gene comprising reacting DNA (a) and DNA (b) hereinbelow in the presence of recombinase Cre and obtaining DNA (c) hereinbelow:
  (a) A DNA comprising of a wild-type loxP site, a gene A and a mutant loxP site according to (1) or (2) above, in this order;

(b) a circular DNA comprising of a wild-type loxP site, a gene B and the same mutant loxP site as DNA (a) in this order; and (c) DNA in which a gene A is replaced by a gene B in DNA (a) wherein each of gene A and gene B is any gene selected from the genes different in each other.

(12) A method for replacing gene comprising reacting DNA (a) and DNA (b) hereinbelow in the presence of recombinase Cre and obtaining DNA (c) hereinbelow:

(a) a DNA comprising of two mutant loxP sites having different nucleotide sequences in each other according to (3) above (mutant loxP site 1 and mutant loxP site 2) and gene A, arranged in the order of mutant loxP site 1/gene A/mutant loxP site 2;

(b) a circular DNA comprising of the mutant loxP site 1, the gene B and the mutant loxP site 2, in this order; and (c) a DNA in which gene A is replaced by gene B in DNA (a) wherein each of gene A and gene B is any gene selected from the genes different in each other.

(13) The method according to (11) or (12) above wherein the gene B is not a functional gene.

(14) The method according to (11) or (12) above wherein the gene A is not a functional gene.

(15) The method according to any one of (11) to (14) above wherein DNA (a) is chromosomal DNA of cells and DNA (b) is plasmid DNA or DNA of DNA of double stranded circular DNA virus.

(16) The method according to any one of (11) to (14) above wherein DNA (a) is chromosomal DNA of cells and DNA (b) has properties to be converted intracellularly to double-stranded circular DNA.

(17) The method according to any one of (11) to (14) above wherein DNA (a) is chromosomal DNA of double-stranded DNA viruses and DNA (b) is plasmid DNA or DNA of DNA of double-stranded circular DNA virus.

(18) The method according to any one of (11) to (14) above wherein DNA (a) is chromosomal DNA of double-stranded DNA viruses and DNA (b) has properties to be converted intracellularly to double-stranded circular DNA.

(19) The method according to (17) or (18) above wherein double-stranded DNA virus of DNA (a) is adenovirus.

(20) A transgenic animal having DNA according to any one of (6) to (9) above on the chromosome.

(21) A pharmaceutical product comprising DNA according to any one of (6) to (9) above.

BRIEF DESCRIPTION OF DRAWINGS

FIG. 2: A synthesized nucleotide sequence of spacer region in mutant loxP site with single-base substitution (sense strand).

FIG. 3: A synthesized nucleotide sequence of spacer region in mutant loxP site with single-base substitution (antisense strand).

FIG. 4: A synthesized sequence of spacer region in mutant loxP site with double-base substitutions (sense strand).

FIG. 5: A synthesized sequence of spacer region in mutant loxP site with double-base substitutions (antisense strand).

FIG. 6: A schematic drawing showing recombinase Cre dependent recombination between mutant loxP sites using linear DNA as substrate. "M": mutant loxP site. Arrow upper part of letter M: direction for loxP site. Numerals: length (bp) of fragment by BsaHI digestion.

FIG. 14: A schematic drawing showing a structure of plasmid pCALwL (D) and plasmid pCALwM (E). CAPro: CAG promoter. GpA: β-globin poly(A) sequence.

FIG. 15: A schematic drawing showing a structure of plasmid puLZM (F) and plasmid puMOL (G). SpA: ori and poly(A) site of SV40.

FIG. 16: A schematic drawing showing a structure of plasmid puLZMOL (H) and plasmid puALZMOL (I). TpA: poly(A) sequence of thymidine kinase.

BEST MODE FOR CARRYING OUT THE INVENTION

Figure 1:
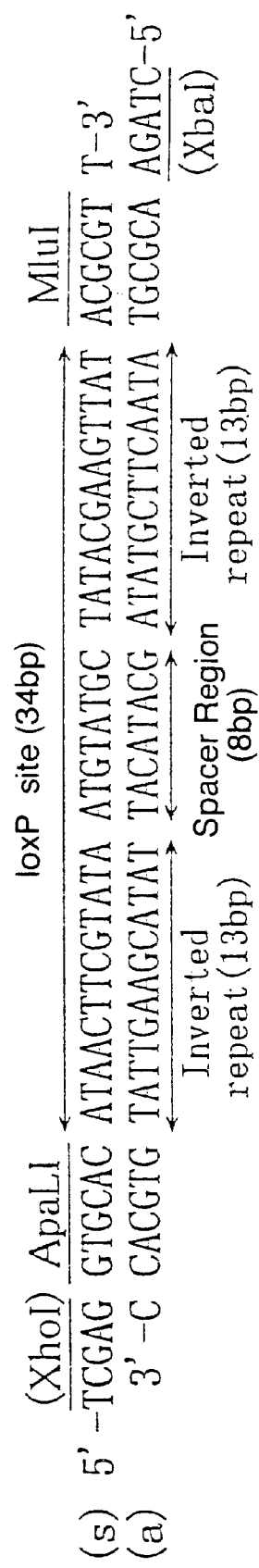
FIG. 1: A structure of synthetic DNA containing wild-type loxP site. (s): sense strand (SEQ ID NO: 55). (a): antisense strand (SEQ ID NO: 56).

The present invention is explained in detail as follows.

The mutant loxP site in the present invention is indicated by the nucleotide sequence, in which specific base(s) in the spacer region of the wild-type loxP site is substituted by base(s) different from original base(s), and as a result of such the substitution, substrate specificity in the specific DNA recombination mediated by recombinase Cre is changed, such the substitution may include substitution of other base(s), which does not affect substrate specificity. The substrate specificity means that, in case of three types of loxP site such as wild-type loxP site, mutant loxP site 1 and mutant loxP site 2, specific DNA recombination mediated by Cre can not substantially occur in combination with the wild-type loxP site and mutant loxP site 1, the wild-type loxP site and mutant loxP site 2, and the mutant loxP site 1 and mutant loxP site 2, respectively. Accuracy of substrate specificity can be a sufficient level to perform gene replacement as described hereinbelow.

The mutant loxP site and the wild-type loxP site are in advance integrated in chromosome of cells, and the circular DNA, in which any gene is located between the same combination of two loxP sites, is transduced into cells together with recombinase Cre. Then, an intermediate, in which four loxP sites are located, is generated as a result of insertion reaction between the respective mutant loxP sites or the respective wild-type loxP sites. Subsequently, the excision reaction occurs between loxP sites which are different combination from the case of insertion reaction, (i.e. in case of the insertion reaction occurring between the wild-type loxP site, the excision reaction occurs between mutant loxP sites). Then the optional gene between the mutant loxP site and wild-type loxP site in the circular DNA is inserted between the mutant loxP site and the wild-type loxP site in the chromosome of cells. In case that another gene is located between the mutant loxP site and wild-type loxP site in the chromosome of cells, such the gene is excised from the chromosome by the above reaction and is replaced by the gene which is inserted in the circular DNA. Consequently, if mutant loxP site and wild-type loxP site exist in the chromosome of cells, any gene can efficiently be inserted into such the site. In addition, instead of a combination with mutant loxP site and wild-type loxP site, two mutant loxP sites, which do not occur specific DNA recombination, can be used.

The mutant loxP site of the present invention was identified as follows.

A mutant loxP site, in which a base at position 7 in the spacer region is substituted from G to A, is known as an example of mutant loxP site, in which substrate specificity of the loxP site is changed. (Hoess et al., Nucleic Acids Res., 14: 2287–2300, 1986). In that assay method, wild-type loxP site and mutant loxP site are ligated into the both sides of kanamycin resistant gene in a plasmid having ampicillin resistant gene and kanamycin resistant gene, then *E. coli* expressing Cre is transformed by the thus obtained plasmid. After selection of ampicillin resistant *E. coli,* the efficiency of the recombination between the wild-type loxP site and mutant loxP site was estimated by the existense of kanamycin resistance (kanamycin resistance is lost, if recombination occurs between two loxP sites). It is uncertain that how much the actual recombination reaction is reflected by the results in such the experiment, because the result of recombination mediated by Cre in one molecule of plasmid is amplified for several hundreds millions times, moreover since it uses drug selection.

We have established more direct and quantitative assay method and identified bases in the loxP site essential for recombination mediated by Cre. Such the assay is explained briefly as follows. DNA containing mutant loxP site with a single-base substitution (total 24 kinds), in which all of 8 bases in the spacer region are substituted by a base one by one selected from all substitutable bases, and DNA containing wild-type loxP site are synthesized by conventional method. DNA fragments, to which the synthesized wild-type loxP site and the mutant loxP site are ligated on both ends of the DNA fragment having suitable length, for example linear DNA fragment prepared by digestion of a plasmid pBR322 by restriction enzyme, are used as substrate. The substrates are reacted with Cre protein in the in vitro cell free system for recombination, then the resulted products are digested by restriction enzyme and electrophoresed to measure quantitatively the efficiency of recombination between the mutant loxP site and the wild-type loxP site. Following results are obtained.

(1) The mutant loxP site, in which base at position 1 or 8 in the spacer region is substituted, can react with the wild-type loxP site.

(2) The reaction between wild-type loxP site and a mutant loxP site, in which base at positions 2, 3, 4 or 5 is substituted, stops almost within intermediate level without progressing to the final stage. A level of progress is slightly different in each other depending on the substituted base position, and in the mutant with substitution at position 5, very small portion proceeds to the final stage.

(3) The reaction between wild-type loxP site and the mutant loxP site with substitution at position 6 can almost not produce intermediate, and the reaction proceeds partially until the final stage. Progression ratio up to the final stage is higher than cases in substitution at position 5 or 7. Progression rate of the reaction is depending on the kind of substituted base.

In case that the original base T is substituted by A, progression ratio up to the final stage is higher than the substitution by C or G.

(4) The reaction between wild-type loxP site and the mutant loxP site with substitution at position 7, can almost not produce intermediate, and the very small part of reaction proceeds to the final stage. The mutant loxP reported conventionally is the substitution of the base at position 7 from G to A. The reaction between wild-type loxP site and mutant loxP site with this substitution, proceeds up to the final stage at about 5% of frequency. This frequency is too high for gene replacement of the present invention. Because, if the recombination between the wild-type loxP site and the mutant loxP site occurs in such high frequency of 5%, a gene between two loxP site (wild-type and mutant type) may possibly be deleted by excision reaction with Cre.

Intermediate used herein means condition of so called Holliday-structure (Hoess et al. Proc. Natl. Acad. Sci., 84:

6840–6844, 1987), in which recombination in one strand of double stranded DNA occurs but the other strand does not. It is known that in the recombination reaction between two loxP sites, after clevage and religation between bases at position 7 and 8 in the lower strand of the spacer region, the reaction is terminated by clevage and religation between bases at position 1 and 2 in the upper strand (Gue et al., Nature, 389: 40–46, 1997). Consequently, substitution of bases at position from 2 to 5 is qualitatively different from the substitution of bases at position 6 and 7. It has become apparent that in the former, the recombination of the lower strand can occur but that of the upper strand can not occur and the reaction stops at the intermediate stage, and in the latter, the recombination of the lower strand occurs partially with the low frequency and the reaction partially proceeds up to the final stage.

Next, using the same assay method, recombination between two mutant loxP sites having identical nucleotide sequence is examined. Although, differences in the efficiency of the reaction in the position of substitution and kind of substituted base is observed, specific recombination mediated by Cre between the two loxP sites with single-base substitution at position from 2 to 7 is confirmed. Difference in efficiency of the reaction depends upon kind of substituted base rather than the position of substitution. For example, substitution of base at position 3 (G) by C, and that of base at position 7 (G) by T are apparently worse in efficiency of the reaction than the substitution by other 2 kinds of base.

Consequently, a mutant loxP site, in which a base selected from a single base at position 2 (T), 3 (G) and 4 (T) in 8 bases of the central part (spacer region) of the wild-type loxP site is substituted by a other base, and DNA having the said mutant loxP site are included within the present invention.

In addition, according to the above knowledge, as a result of a combination of more than two of the single base substitution, which is qualitatively different each other, i.e. a combination of the substitution in any one base at position from 2 to 5 and the substitution at position 6 or 7, it is expected to be able to obtain the mutant loxP site, which has extremely high specificity than single base substitution and has recombination efficiency between two identical mutant loxP site almost equal to the single base substitution.

Then, using the mutant loxP sequence, in which a base substitution in any one of bases at position from 2 to 5 and a base substitution at position 7 are combined, and efficiencies of recombination between the wild-type loxP site and the mutant loxP site, and between two identical mutant loxP sites, are examined. As a result, the recombination between wild-type loxP site and most of the mutant loxP site with double-base substitutions can not proceed entirely up to the final stage. Consequently substrate specificity of double-base substitutions mutant is obviously increased as compared with the single-base substitution mutant. However, the efficiency of the recombination between the identical two mutant loxP sites is largely different depending on their substitutions. Namely, some mutant loxP sites can not react with the wild-type loxP site. Following mutant loxP sites show practically sufficient recombination efficiency: T2C/G7A (#2171, SEQ ID NO: 26), T2A/G7A (#2271, SEQ ID NO: 29), T2A/G7C (#2272, SEQ ID NO: 30), G3A/G7A (#3171, SEQ ID NO: 35), G3T/G7A (#3371, SEQ ID NO: 39), T4C/G7A (#4171, SEQ ID NO: 42) and A5G/G7A (#5171, SEQ ID NO: 49). Among them, reaction efficiency of T2A/G7C (#2272) and A5G/G7A (#5171) is extremely high. Numerals show a position of substituted base. A base before the numeral shows a pre-substituted base and a base after the numeral shows a post-substituted base. For example, abbreviation T2C/G7A means that a base at position 2 to substituted from T to C, and a base at position 7 is substituted from G to A. Relationship between number and SEQ ID NO in a parenthesis is shown in Table 2 hereinafter.

As indicated, the recombination between the wild type loxP site and the mutant loxP site, in which two bases in spacer region of the wild-type loxP site are simultaneously substituted can not occur, but the recombination reaction between two mutant loxP sites can occur with high efficiency, which is apparently showed that the substrate specificity of the mutant loxP site with double-base substitutions is more increased than the loxP site with single-base substitution.

Consequently, the mutant loxP site, in which at least one base at position 2 (T), 3 (G), 4 (T) and 5 (A), and at least one base at position 6 or 7 in 8 bases in the central part (spacer region) of the wild type loxP are substituted by other base, and DNA having the said mutant loxP site are included in the present invention.

We have also examined whether the recombination between the mutant loxP site having different nucleotide sequence can occur or not. T2C/G7A (#2171) and T2A/G7C (#2272) are exemplified for that case, however no recombination can occur between these two types of different mutant loxP sites. This fact means that at least three types of loxP sites having different substrate specificities, i.e. the wild-type loxP site, the mutant loxP site 1 and the mutant loxP site 2, are found and are preferable for gene replacement hereinbelow described.

A method for gene replacement using the mutant loxP site of the present invention and application thereof are explained as follows.

The method for gene replacement of the present invention is comprised of: reacting with DNA (a) containing of the wild-type loxP site, gene A and the mutant loxP site, in this order, and circular DNA (b) containing of the wild-type loxP site, gene B and the mutant loxP site, in this order, in the presence of recombinase Cre, and replacing the gene A to the gene B in DNA (a). In this case, recombination dependent on Cre between the wild-type loxP site and the mutant loxP site can not occur, and gene A and gene B are any genes which are different in each other.

The method for gene replacement of the present invention is comprised of: reacting DNA (a) containing of two mutant type loxP sites having each different nucleotide sequences (mutant loxP site 1 and mutant loxP site 2) and gene A arranged in the order of the mutant loxP site 1/the gene A/the mutant loxP site 2, and circular DNA (b) containing of the mutant loxP site 1, the gene B and the mutant loxP site 2, in this order in the presence of recombinase Cre, and replacing gene A to gene B in DNA (a).

In this case, recombination dependent on Cre between the mutant loxP site 1 and the mutant loxP site 2 can not occur, and gene A and gene B are any genes which are different in each other.

The method for gene replacement will be performed basically as follows. As for example, the method using the wild-type loxP site and the mutant loxP site is explained, but a case using the mutant loxP site 1 and the mutant loxP site 2 is same as in the case hereinabove. Explanation will be given with the case for replacement of gene in chromosome of animal cells, however the method of the present invention can be applied for not only in chromosome of animal cells but also genome of animal virus, plant cells, chromosomes of microorganisms such as yeast and bacteria and bacteriophage.

First of all, the wild-type loxP site and the mutant loxP site are in advance integrated into chromosome of animal cells.

The gene A can optionally be located between the wild-type loxP site and the mutant loxP site, and in this case gene replacement will be applied and if no gene A exists, the gene insertion technique will be applied.

Reversely, the gene B to introduce is inserted between two loxP sites in a circular DNA molecule, in which the wild-type loxP site and the mutant loxP site are inserted. The circular DNA molecule can be a already circularized molecule such as plasmid DNA and DNA of DNA of double-stranded circular DNA virus, or a molecule which may be converted to circular molecule by any operation after transfected into cells. The circular DNA molecule, in which the gene B, the wild-type loxP site and the mutant loxP site are located, is transfected into cells previously mentioned by means of known method, and simultaneously Cre protein is expressed in that cells, then the gene B in the circular DNA molecule is integrated between the wild-type loxP site and the mutant loxP site on the chromosome of the cells. In case that the gene A is located between two loxP sites on the chromosome of cells, the gene replacement, in which the gene A is excised and the gene B is inserted, occurs. In case that no gene is located between two loxP sites on the chromosome, gene insertion occurs. Further, if no gene is located between two loxP sites in the circular DNA, gene A on the chromosome can be excised. Furthermore, even in case that no gene A exists, since two lox P sites are existed on the chromosome, another gene can also be inserted between two loxP sites by using the other circular DNA molecule which has optional gene C between two loxP sites.

Conventional method for transfection of circular DNA molecule in animal cells can be used. Examples are physicochemical methods such as electoporation, calcium phosphate transfection, DEAE-dextran transfection, lipofection and gene gun, and using circular DNA virus. Examples of circular DNA virus are papilloma virus and SV40. Example of method for converting to circular molecule after introduction into cells is a method using recombinase, examples of which are FLP derived from 2 $\mu$l plasmid of yeast, R derived from pSR1 plasmid of *Zygosaccharomyces rouxii* and Cre.

In order to integrate two loxP sites into chromosome of animal cells precendently, for example, cells are transformed by using plasmid DNA having two loxP sites. Transfection of gene in the transformation can be carried out by previously mentioned physico-chemical methods. Further, viruses having properties to integrate viral genome into chromosome of cells, such as retrovirus, adeno-associated virus and HIV can also be used.

Methods for expressing Cre in animal cells are, for example, a method for expressing Cre protein in cells after transfection of DNA or RNA encoding Cre gene into cells, or a method of introduction of Cre protein itself into cells. Example in the former is a physicochemical method for transfection of DNA or RNA encoding Cre gene into cells, and a method of using virus vector. Examples of virus vectors are adenovirus, vaccinia virus, helpes virus and EB virus. Among them, adenovirus is preferable example due to high efficiency of gene transfer.

Advantages of the gene replacement on chromosome of animal cells using mutant loxP site of the present invention are high efficiency of the gene replacement and possibility of insertion of the gene for specific location of chromosome. The latter is especially important for obtaining transformant. Because, in methods of conventional transformation using DNA (except for homologous recombination) or virus vector such as retrovirus and adeno-associated virus, since the objective gene is integrated into chromosome at random, the level of expression of the objective gene and its stability in chromosome are varied largely depending on integrated sites. Therefore, for example, in order to obtain transformed cell line, which can stably express the objective gene with high level for long period, large number of cell lines have to be screened and selected. Furthermore, the screening has to be repeated in each gene, i.e. in each transformation. Contrary to that, in a method of the present invention, if it is once obtained stable cell lines with high level expression of the gene between two loxP sites as an index of the gene expression, even though any gene is introduced to the cell lines, it can be easy to obtain a stable cell line with high level expression of the gene introduced. Furthermore, since the efficiency is very high, no operation for drug selection, which is conventionally essential operation, is required, and the objective cell lines can be obtained within short time only by cloning operation of cells. Though there is no specific restriction for the objective cells, it is most preferable for the purpose of transformation of ES cells used for generation of transgenic animals.

The gene replacement of chromosome of animal cells according to the present invention can be applied for not only cultured cells but also whole animal. As for a method for expressing specific foreign gene in animal body, a technique of transgenic animal is known. However, generation of transgenic animal which expresses objective gene needs for long time. In order to generate transgenic animals by common methods, very complex operations are necessary, i.e. preparing ES cells for expressing objective gene, developing the ES cells in pseudopregnant maternal oviduct, screening the fetus by means of an index of expression of the objective gene to obtain transgenic animals, mating animals expressing objective gene. The operations require generally for half to one year. Using the method of the present invention, once transgenic animals for gene transduction are generated, generation of transgenic animals corresponding to respective genes is not required. The transgenic animals for gene transduction are animals, in which the mutant loxP site and the wild-type loxP site are integrated into chromosome. The generation of such animals can be performed by the same method as in generation of conventional trangenic animals. Drug resistant gene such as neomycin resistant gene may be inserted between two loxP sites for drug selection. To the animals for gene transduction, as a result of transduction of (a) circular DNA molecule, in which the objective gene is inserted between the wild-type loxP site and the mutant loxP site and (b) Cre protein, the objective gene is inserted into chromosome in tissues or cells, in which both of (a) and (b) are transduced, and the gene can be expressed. Introduction of (a) and (b) into animal body can be sufficiently carried out by conventional methods such as liposome, virus vector and gene gun. Using the method of the present invention, in case that different gene is transduced, circular DNA molecule (a) depending on gene is only used and generating transgenic animals, which requires for long time, is no more necessary. Further, by only transducing both of (a) and (b) locally, the objective gene can be inserted into only the target organs or tissues.

The present invention can be applied for generation of recombinant virus. Example of virus is DNA virus. Examples of DNA viruses are adenovirus, herpesviruses such as herpes simplex virus, EB virus, cytomegalovirus, and poxviruses such as vaccinia virus, canarypox virus and insect baculovirus. Further example is RNA virus, and especially retrovirus is preferable. Because, in case of preparing retrovirus vector, potential virus producing cells are selected for respective retrovirus vectors, which produce respective genes. Using the present method, once high potential virus producing cell lines, which express marker gene, are established, highly productive cell lines can easily be obtained by replacing the marker gene on the chromosome of cell lines to the objective gene.

Concrete example of preparing recombinant virus of the present invention is explained in an example of generating recombinant adenovirus. Conventional method for generating recombinant adenovirus is: transforming cells such as 293 cell by means of plasmid vector or cosmid vector, to which adenovirus genome and objective gene are inserted, after cloning the recombinant virus generated by homologous recombination, selecting the objective virus and proliferating the virus. This needs for long time operation. According to the method of the present invention, since the operation does not use low efficient homologous recombination, the objective recombinant virus can be generated within short time. Namely, at first, adenovirus for gene transduction, to which the mutant loxP site and the wild-type loxP site are inserted, is generated, then the said virus is infected to cells such as 293 cells preferable for generation of recombinant adenovirus. Simultaneously, the plasmid DNA, to which the objective gene is inserted between the wild-type loxP site and the mutant loxP site, is transduced into the said cells and Cre protein is expressed. As a result, the recombinant virus, to which the objective gene is inserted between the wild-type loxP site and the mutant loxP site, can be obtained with high frequency. In this case, process may include that adenovirus for gene transduction is generated in order to be deleted the packaging signal between the loxP sites by recombination mediated by Cre, and the objective gene and packaging signal from plasmid DNA are simultaneously added and replaced to obtain the objective virus selectively. Cre protein may be transduced in the form of plasmid DNA, or supplied by cells which can express Cre protein constitutively or inducibly by any induction after cells are previously transformed.

The above method is explained in detail as follows. Explanation is given in case of generating recombinant adenovirus in which a foreign gene A is replaced by a foreign gene B. Example of a structure of recombinant adenovirus for gene transduction is adenovirus in which loxP sites are inserted in the order of adenovirus left inverted terminal repeat (ITR)/wild-type loxP site/packaging signal/wild-type loxP site/gene A/mutant loxP site. A fragment of wild-type loxP site/gene A is inserted into E1 deletion region. Example of plasmid DNA for insertion of foreign gene B is a plasmid having structure of wild-type loxP site/packaging signal/gene B/mutant loxP site. These adenovirus for gene transduction and plasmid for foreign gene B insertion are simultaneously or sequentially transduced into cells such as 293 cells, which can express Cre protein, then the packaging signal between two wild-type loxP sites in adenovirus for gene transduction is excised, and at the same time, the recombinant adenovirus, in which a region of wild-type loxP site/gene A/mutant loxP site is replaced by the portion of wild-type loxP site/packaging signal/gene B/mutant loxP site derived from the plasmid, is generated. Adenovirus for gene transduction which did not occur gene replacement, can replicate viral DNA, but can not replicate virus itself, since the packaging signal is deleted by an action of usual "excision reaction" having high reaction efficiency between two wild-type loxP sites and DNA can not packaged within virus particles (virion). On the contrary, gene replaced adenovirus has packaging signal, consequently the adenovirus can replicate as virus and the recombinant adenovirus which is replaced by "gene B" can be obtained with high frequency.

Insertion position of the mutant loxP site in adenovirus for gene transduction can be proximal to the foreign gene A, or may be a position within adenovirus genome distal to the foreign gene A. Examples of position of insertion in the latter are untranslated region between L3 gene and E2A gene, deletion site of E3 gene and a region between upstream region of E4 gene and right ITR. In case that the mutant loxP site is inserted into any of these regions to perform gene replacement, length of DNA between wild-type loxP site/mutant loxP site in the plasmid for gene insertion has to be adjusted, in order to effectively packaging the generated adenovirus DNA into the virus particles (virion). However, since the gene replaced recombinant adenovirus is deleted essential gene for virus replication, adverse reactions which are problems of the present adenovirus may be reduced, in case of using as a gene therapy vector.

DNA containing mutant loxP site of the present invention can be used for gene therapy as pharmaceuticals. The method is explained as follows.

At first, the mutant loxP site and wild-type loxP site are in advance integrated into chromosome of human cells. To this end, DNA having mutant loxP site and wild-type loxP site is used for pharmaceuticals. The said DNA is administered, for example in the form of containing within virus vector such as retrovirus and adeno-associated virus (AAV). Among them, AAV is preferably used. Because, the gene transferred by retrovirus is integrated randomly into chromosome, but it is probable that the gene is integrated into the specific region in chromosome (AAV-S1 region in chromosome 19) with high frequency in the case of gene transfer by AAV. The viral gne encoded by AAV (Rep) is prerequisite for gene integration into the specific region in chromosome. Since large part of AAV gene is deleted in the AAV vector presently used, specific integration mechanism into chromosome is deleted. Due to the reason that however, as the length of sequence added with mutant loxP site and wild-type loxP site is less than 100 bp, it is possible to construct the virus, to which two loxP sites are inserted and retains whole viral gene of AAV. The insertion site of loxP site is preferably just inside of the inverted terminal repeat (ITR) located both ends of AAV gene. As a result of administration of AAV inserted with two loxP sites into human, two loxP sites can be integrated into chromosome.

Further, a pharmaceutical preparation containing circular DNA, to which the objective gene is inserted between wild-type loxP site and mutant loxP site, and Cre protein or DNA molecule encoding Cre gene are administered, then AAV gene between two loxP sites located in the chromosome is deleted and replaced by the objective gene. Administration of circular DNA and Cre protein or DNA molecule encoding Cre gene as pharmaceuticals into human cells can be made by a method using vectors used for conventional gene therapy such as virus vector and liposome vector.

In the human cells integrated the objective gene into chromosome as such, wild-type loxP site and mutant loxP site are located in both end of the objective gene, and only ITR of AAV is located outside thereof, there is no structural gene of AAV, consequently proteins derived from AAV do not express nor become antigen, and it is expected that the expression of the objective gener continue for a long period stably. If the integrated gene is no more necessary, the gene can be deleted from the chromosome by administration of circular DNA which has no gene between wild-type loxP site and mutant loxP site. Further, if it become necessary to integrate a gene into the chromosome again, since two loxP sites remain on the chromosome, any gene can be integrated by a method described hereinbefore. As explained, DNA having mutant loxP site of the present invention can be used as pharmaceuticals for gene therapy, by which integration of gene into chromosome and excision therefrom can freely be performed.

In case that DNA having mutant loxP site of the present invention is used as pharmaceuticals, transduction of the said DNA into cells can be made by means of virus vector and others (Nikkei Science, April, 1994, pp 20–44, Monthly Pharmaceuticals, 36(1): 23–48, 1994, and cited references therein). Any means can be used in the present invention.

Examples of transduction using virus vector are methods for inserting DNA containing mutant loxP site of the present invention or corresponding RNA into viruses such as retrovirus, adenovirus, adeno-associated virus, herpesvirus, vaccinia virus, poliovirus, RNA viruses such as sindbis virus and the like. Among them, methods using retrovirus, adenovirus and adeno-associated virus are most preferable.

Examples of other method for transduction are liposome, lipofectin, micro injection, calcium phosphate transfection, electroporation and gene gun, and the liposome is most preferable.

In the practical application of DNA having mutant loxP site of the present invention as pharmaceuticals, in vivo method, in which the said DNA is directly injected into body and ex vivo method, in which some kind of cells are collected from human body and the said DNA is transduced into the said cells in vitro, then the cells are returned to the body, are known (Nikkei Science, 1994 April, pp 20–45, and Monthly Pharmaceuticals, 36(1): 23–48, 1994, and cited references therein). In the pharmaceuticals of the present invention, any method can be selected and applied depending on diseases for treatments and target organs.

In case that the pharmaceuticals of the present invention are administered in vivo, suitable administration route can be selected for administration considering disease for treatments and target organs. For example, administration can be made intravenously, intraarterialy, subcutaneously or intramuscularly, or directly administered into organs of diseases such as kidneys, liver, lungs, brain and nerves.

Administration ex vivo can be made according to the conventional methods that human cells (for example lymphocytes and hematopoietic stem cells) are collected, and pharmaceuticals of the present invention are sensitized with them for gene transduction, then the cells are returned into human body.

In case that in vivo methods are selected, various pharmaceutical formulations (for example, solutions) can be used, and generally injection containing DNA having mutant loxP site as an active ingredient is applied. If necessary, conventional carrier can be added. Such the injections can be prepared by conventional methods. For example, after DNA having mutant loxP site is dissolved in suitable solution (for example, steriled water, buffer, saline, and the like), the solution is filtered for sterilization then filled in aseptic vessels. In replace of DNA having mutant loxP site, virus vector inserted with DNA containing mutant loxP site can be formulated. Further, liposome (or HJV-liposome) encapsulated with DNA having mutant loxP site can be a formulation of liposome preparation such as suspension, freezing preparation and centrifuged concentrated freezing preparation.

Contents of DNA having mutant loxP site can be formulated depending upon type of diseases for treatments, target organs, age of patients and body weight, and are 0.0001 mg–100 mg, preferably 0.001–10 mg, as conventional DNA having mutant loxP site, and are administered once within several days to several months.

The above explained are method of gene replacement using two loxP sites including a combination of wild-type loxP site and mutant loxP site or a combination of mutant loxP site 1 and mutant loxP site 2. Application area for gene replacement can be extended by using more than three loxP sites having different substrate specificities. Examples of a combination of three loxP sites having different substrate specificities are the combination of wild-type loxP site and two mutant loxP sites or the combination of three mutant loxP sites. A method in case that three different loxP sites including wild-type loxP site, mutant loxP site 1 and mutant loxP site 2 are existed on the identical DNA is explained. DNA (a) having wild-type loxP site/gene A/mutant loxP site 1/gene B/mutant loxP site 2, in this order, and circular DNA (b) having wild-type loxP site/gene C/mutant loxP site 1 are reacted in the presence of ricombinase Cre, then gene A in DNA (a) can be replaced by gene C. Contrary to that, instead of the circular DNA (b), DNA (c) having mutant loxP site 1/gene D/mutant loxP site 2 and DNA (a) are reacted in the presence of ricombinase Cre, then gene B in DNA (a) can be replaced by gene D. Namely, it is possible to replace a desired gene among multiple genes in DNA (a) with the optional gene by using only different circular DNA.

Concrete examples of gene replacement using mutant loxP site of the present invention are explained. In the all following embodiments, the mutant loxP site, in which a base at position 2 in the spacer region is substituted from T to C and a base at position 7 is substituted from G to A (SEQ ID NO: 26), is used as a mutant loxP site.

(1) Replacement of Gene in Adenovirus Genome

Example of replacing gene is *E. coli* lacZ gene. A lacZ gene on the circular DNA molecule is inserted between wild-type loxP site and mutant loxP site in adenovirus genome. Effectiveness of mutant loxP site of the present invention can be confirmed by this system.

At first, adenovirus to be gene replaced, i.e. adenovirus for target, was constructed. Namely, we constructed recombinant adenovirus (AxCALwM), in which CAG promoter/wild-type loxP site/mutant loxP site/poly(A) sequence was inserted in the left direction for transcription (reverse direction of transcriptional direction for adenovirus E1 gene) in the E1 gene deletion site of adenovirus type 5, in which E1 gene and E3 gene were deleted. CAG promoter herein used is a high expression vector disclosed in Japanese Patent Unexamined Publication No. Hei 3-168087.

Circular DNA molecule, in which lacZ gene was inserted between the wild-type loxP site and the mutant loxP site, may optionally be transduced into cells directly by transfection as plasmid DNA having structure of wild-type loxP site/lacZ gene/mutant loxP site. However, gene transfer efficiency into cells by the transfection was only several tens per cents, and the objective gene could not transducted into all of cells, consequently a method by Cre-dependent intracellular formation of circular DNA using adenovirus vector was applied and as a result, circular DNA could be transduced into almost all cells. To that end, we constructed recombinant adenovirus (AxALZMOL), in which poly(A) sequence of thymidine kinase (TK) gene of herpes simplex virus/wild-type loxP site/lacZ gene/mutant loxP site/ori and poly(A) sequence of SV40/wild-type loxP sequence were inserted into E1 gene deletion site of adenovirus type 5 in the left direction of the transcriptional direction. The thus constructed recombinant virus AXALZMOL is designated as adenovirus for donor. Recombination can occur between two wild-type loxP sites by an action of Cre protein on AXALZMOL, and circular DNA molecule having a structure of wild-type loxP site/lacZ gene/mutant loxP site ori and poly(A) sequence of SV40 was generated. Poly(A) sequence of TK lgene was inserted for preventing of the transcription of lacZ gene from unidentified promoter derived from adenovirus. Cre protein was supplied by using recombinant adenovirus AxCANCre expressing Cre (Kanegae et al., Nucleic Acids Res., 23: 3816–3821, 1995).

Experiment on replacement (insertion) on gene in adenovirus genome was conducted using these three recombinant adenoviruses. Adenovirus AxALXMOL for donor, adenovirus AxCALwM for target and adenovirus AxCANCre expressing Cre were simultaneously infected in animal cultured cells (CV-1 cells or COS-1 cells). Both adenovirus for donor AxALZMOL and generated circular DNA molecule have lacZ gene, but have no promoter, consequently lacZ gene can not be expressed. The lacZ gene can only be expressed when lacZ gene in the circular DNA molecule is inserted into the downstream of CAG promoter in adenovirus AxCALwM for target, i.e. between wild-type loxP site and mutant loxP site. Consequently, expression of lacZ gene is the obvious evidence for actual gene replacement (in this case, insertion).

There were no cells expressed lacZ gene when cells were infected with each of the above three viruses alone or with combinations of two viruses among them. The expression of lacZ gene was observed clearly when cells were simultaneously infected with these three viruses, furthermore ratio of cells expressing lacZ gene was increased depending on amount of adenovirus for donor and at maximum 90% of cells showed lacZ gene expression. These results showed that lacZ gene on adenovirus for donor was inserted with very efficiently between wild-type loxP site and mutant loxP site in adenovirus for target through the formation of circular DNA molecule, namely occurrence of gene replacement.

(2) Replacement of Gene in Chromosome of Animal Cells

Following experiments were conducted in order to show the fact that not only gene on adenovirus but also gene on chromosome of animal cells can be replaced effectively. Principles of the experimental system are same as in (1). In order to obtain cell lines (target cells) to be replaced by a gene, CV-1 cells were transfected with the plasmid containing DNA bearing a structure of CAG promoter/wild-type loxP site/hygromycin B resistant gene/mutant loxP site/poly (A) sequence, then hygromycin resistant cell lines, inserted with only single copy of DNA bearing the above structure in a cell, were established.

These cell lines were simultaneously infected with adenovirus AxALZMOL for donor and Cre expressing adenovirus AxCANCre. As a result, although there were no lacZ gene expressing cells infected with adenovirus for donor or Cre expressing adenovirus alone, however, lacZ gene expressing cells were observed with high frequency when cells were doubly infected with these viruses. Proportion of lacZ gene expressing cells were different depending on cell lines used, and lacZ gene were expressed at maximum approximately 30% of cells. Since cloning of cells did not perform in this experimental system, proportion of cells expressing lacZ gene shows directly ratio of gene replacement on the chromosome. Consequently, the above result indicates that gene replacement on the chromosome of animal cells can be performed with very high efficiency by using the loxP site of the present invention.

The present invention will be explained in detail by showing examples as a part of the present invention. The present invention is not limited by these examples and conventional modification in the technical field of the present invention can naturally be applied to the present invention. Various operations and treatments on phages, plasmids, DNA, E. coli and cultured cells in examples were performed, if not specified, according to methods described in "Molecular Cloning, A Laboratory Manual, T. Maniatis et al. Ed., 2nd Ed. (1989), Cold Spring Harbor Laboratory.

EXAMPLE 1

Recombinase Cre Dependent Recombination Reaction Between Two Mutant loxP Sites (1) Preparation of Cell Extract Containing Recombinase Cre Following operations were performed in order to obtain cell extract containing Cre for use of recombinase Cre dependent recombination reaction. 293 cells (cell line derived from human fetal kidney) in a 225 $cm^2$ flask were infected (37° C., 1 hour) with approx. $1\times10^9$ PFU of Cre expressing recombinant adenovirus vector AxCANCre (Kanegae et al., Nucleic Acids Res., 23: 3816–3821, 1995). Medium (DMEM medium, containing 5% FCS) was further added thereto, and cultured for 24 hours. After cultivation, cell suspensions were centrifuged by low speed centrifuge at 1000 rpm for 5 minutes, and the cultured supernatant was discarded to collect cells. Cells were suspended by adding 5 ml of storage buffer [50% glycerol/20 mM Tris-HCl (pH 7.5)/300 mM NaCl/1 mM EDTA (pH 7.5)], sonicated using closed type sonicator at 200W for 2 minutes (30 sec.×4) and released intracellular Cre protein. The thus obtained cell sonicated fluid was centrifuged by using micro centrifuge at 15000 rpm for 10 minutes, and the supernatant was stored in freezing (−80° C.).

(2) Preparation of Synthetic DNA Containing Mutant loxP Site

Synthetic DNAs consisting in each of 52 bases, in which 8 bases of the spacer region in the wild-type loxP site were substituted in one base or simultaneously two bases by other bases, were prepared. Types of the synthesized DNA were, 24 types for one base mutation and 29 types for two bases simultaneous mutation, and respective sense strand and antisense strand were synthesized. Structure of synthetic DNA of wild-type loxP site is shown in FIG. 1 (sense strand: SEQ ID NO: 55, antisense strand: SEQ ID NO: 56). The sequences of mutant loxP sites (sense strand and antisense strand) are shown in FIG. 2–FIG. 5. The sense and antisense strands of the wild-type loxP site are not completely complementary sequences. These were designed that when each strand was annealed to prepare double stranded DNA, 4 bases were respectively protruded at 5' end to form the digestion fragments of restriction enzymes XbaI and XhoI. To this end, these double stranded DNA can be ligated with digestion fragments of restriction enzymes XbaI and NheI in XbaI fragment side and digestion fragments of restriction enzymes XhoI and SalI in XhoI fragment side, respectively.

All of the single stranded synthetic DNAs were kinased at 5' end with T4 polynucleotide kinase, and sense and antisense strands corresponding to respective mutations were annealed. These double stranded synthetic DNA is hereinafter designated as mutant loxP synthetic DNA.

(3) Preparation of Substrate DNA Containing Two Mutant loxP Sites

Following operations were conducted in order to obtain substrate DNA containing mutant loxP site with identical sequence in both ends of linear DNA.

Plasmid pBR322 was doubly digested with restriction enzymes NheI and SalI, and ligated with each of twenty-four mutant loxP synthetic DNA (single-base substitution) by T4 DNA ligase (plasmid:synthetic DNA, molar ratio 1:6) and digested doubly by restriction enzyme XbaI and XhoI. Mutant loxP synthetic DNA, which is bound with plurally both ends of pBR322 DNA, is deleted by the restriction enzyme treatment, and the linear DNA, approx. 4.1 kb, in which two mutant loxP synthetic DNAs, having identical sequence are ligated at the both ends of pBR322 DNA, is produced. Unreacted and restriction enzyme digested mutant loxP synthetic DNA were removed by using GEANCLEAN II (Funakoshi Inc.) to obtain the linear DNA (approx. 4.1 kb) ligated with mutant loxP site at the both ends, which is used in the following reaction as substrate DNA.

(4) Cre Dependent Recombination Reaction Between Two Mutant loxP Sites

It was examined whether Cre dependent recombination reaction between two mutant loxP sites occurs or not by the following assay method.

Substrate DNA (1 μg) prepared in (3) and cell extract containing Cre (10 μl) prepared in (1) were incubated at 37° C. for 30 min in a 50 μl volume of buffer containing 50 mM Tris-HCl (pH 7.5)/10 mM MgCl2/1 mg/ml bovine serum albumin/1 mM phenylmethylsulfonyl fluoride (PMSF)/5 μg/ml aprotinin. After completion of the reaction, 45 μl of TE buffer (pH 8.0) and 5 μl of EDTA solution (pH 8.0) were added to the reaction mixture, extracted with phenol/chloroform and with chloroform, followed ethanol precipitation. The recovered DNA was dissolveld in 30 μl of TE buffer (pH 8.0) containing RNase A (20 μg/ml). Half volume thereof was digested with restriction enzyme BsaHI. The DNA bands detected by ethidium bromide (EtBr) staining after agarose gel electrophoresis, were analyzed.

Before recombination mediated by Cre, restriction enzyme BsaHI digestion of linear substrate DNA (approx. 4.1 kb) generates four bands of 2.7 kb, 610 bp, 380 bp and 360 bp. On the other hand, as a result of recombination of substrate DNA mediated by Cre, a circular DNA of approx. 4.0 kb containing one mutant loxP, and a linear DNA of approx. 50 bp consisting of only mutant loxP, are produced. Digestion of these DNA with restriction enzyme BsaHI generates four bands of 2.7 kb, 920 bp, 380 bp and 50 bp (refer to FIG. 6). Consequently, since band of 920 bp indicates that recombination mediated by Cre has occurred, and bands of 610 bp and 360 bp indicate that recombination mediated by Cre has not occurred, the ratio of the density of these bands indicates efficiency of recombination reaction. Results are shown in Table 1.

TABLE 1

Cre-dependent Recombination Reacitons between Wild-type loxP Site and Mutant loxP Site (Single Base Substitution)

| SEQ ID NO. | Synthetic DNA NO | Mutant loxP Site - Mutant loxP Site | | Wild-type loxP Site - Mutant loxP Site | |
|---|---|---|---|---|---|
| | | Intermediate (970 bp) | Final Product (920 bs) | Intermediate (970 bp) | Final Product (920 bp) |
| 1 | wild | 1 | 9 | 1 | 9 |
| 2 | #11 | 4 | 2 | 3 | 5 |
| 3 | #12 | 6 | 3 | 4 | 7 |
| 4 | #13 | 4 | 3 | 3 | 7 |
| 5 | #21 | 4 | 5 | 5 | 0 |
| 6 | #22 | 4 | 5 | 7 | 0 |
| 7 | #23 | 6 | 5 | 9 | 0 |
| 8 | #31 | 5 | 7 | 9 | 0 |
| 9 | #32 | 6 | 3 | 9 | 0 |
| 10 | #33 | 6 | 6 | 9 | 0 |
| 11 | #41 | 1 | 7 | 9 | 0 |
| 12 | #42 | 5 | 6 | 9 | 0 |
| 13 | #43 | 5 | 6 | 9 | 0 |
| 14 | #51 | 1 | 9 | 7 | 1 |
| 15 | #52 | 1 | 9 | 7 | 2 |
| 16 | #53 | 1 | 8 | 7 | 1 |
| 17 | #61 | 1 | 8 | 1 | 3 |
| 18 | #62 | 1 | 8 | 1 | 6 |
| 19 | #63 | 1 | 9 | 1 | 2 |
| 20 | #71 | 1 | 7 | 1 | 1 |
| 21 | #72 | 3 | 7 | 1 | 1 |
| 22 | #73 | 3 | 1 | 1 | 1 |
| 23 | #81 | 3 | 3 | 4 | 7 |
| 24 | #82 | 8 | 5 | 5 | 9 |
| 25 | #83 | 2 | 9 | 2 | 8 |

[In the table, amounts of reaction intermediates and final products were indicated in 10 grades with 0–9. Larger number indicated larger amount of production. Amount of final reaction product (density of DNA bands) in case of reaction between two wild-type loxP site was set as maximum numeral "9", and in case of no DNA band was detected (less than 5% of "9"), the result was set as "0". Details of reaction intermediates will be explained in example 2-(2).]

The recombination efficiencies between two identical mutant loxP sites #11 and between #73 were low. It was confirmed that the recombination between other respective identical mutant loxP sites mediated by Cre had occurred, although slight differences in the efficiency of recombination are observed depending on their sequences.

EXAMPLE 2

Cre-dependent Recombination Between Wild-type loxP Site and Mutant loxP Site (No. 1)

(1) Preparation of Substrate DNA Containing Wild-type loxP Site and Mutant loxP Site

[1] Construction of Plasmid (pBRwt) Containing One Wild-type loxP Site

Following operations (a) and (b) were conducted in order to construct plasmid (pBRwt) inserted one wild-type loxP site into plasmid pBR322.

(a) pBR322 was digested with restriction enzyme EcoNI, blunt-ended with Klenow enzyme and extracted with phenol/chloroform to denature EcoNI and Klenow enzyme, then the reaction mixture was substituted to TE buffer by gel filtration. EcoNI digested pBR322 was ligated with XhoI linker (5'-pCCTCGAGG-3'), doubly digested with restriction enzymes XhoI and PstI, then DNA band of approx. 2.9 kb was excised from the agarose gel after electrophoresis. The DNA band was purified using GEANCLEAN II (Funakoshi Inc.) and the DNA fragment of approx. 2.9 kb having XhoI digested fragment in one end and PstI digested fragment in the other end was obtained.

(b) pBR322 was digested with restriction enzyme NheI, ligated the synthetic DNA (52 bp) containing wild-type loxP site, and doubly digested with restriction enzymes XhoI and PstI. After agarose gel electrophoresis, the DNA band of approx. 1.4 kb containing a wild-type loxP site, was excised from the gel and purified using GEANCLEAN II (Funakoshi Inc.). The DNA fragment of approx. 1.4 kb, has also XhoI digested fragment in one end and PstI digested fragment in the other end.

After both of DNA prepared in (a) and (b) were ligated, E. coli was transformed to obtain plasmid pBRwt (4.4 kb, FIG. 7), to which one wild-type loxP site was inserted between NheI site and EcoNI site of pBR322.

[2] Preparation of Substrate DNA Containing Wild-type loxP Site and Mutant loxP Site Following operations were conducted in order to prepare substrate DNA having wild-type loxP site in one end and mutant loxP site in the other end of linear DNA.

Figure 8:
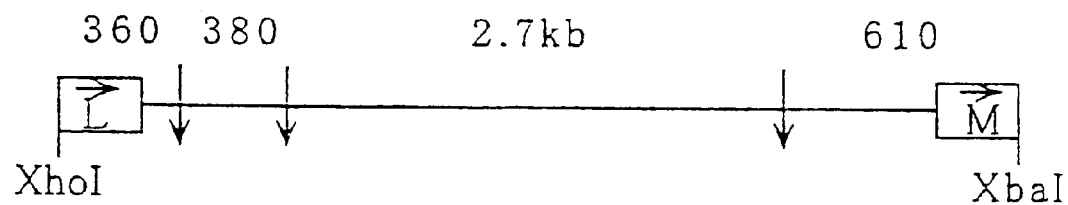
FIG. 8: A schematic drawing showing a linear DNA in which a wild-type loxP site in one end and a mutant loxP site in other end are bound. "M": mutant loxP site. "L": wild-type loxP site. Arrow upper part of letter: direction for loxP site. (the same as in the figures hereinbelow). Arrow for downward direction: BsaHI site. Numerals show length (bp) of BsaHI digestion fragment.

SalI site was located in a position about 30 bp distance from wild type loxP site in plasmid pBRwt, pBRwt was digested with restriction enzyme SalI to prepare linear DNA. SalI digested pBRwt was ligated with the mutant loxP synthetic DNA (52 bp, 24 kinds), which was the same DNA as of example 1-(3), (plasmid: synthetic DNA, molar ratio 1:6). As a result of this operation, XhoI digested fragment side of the mutant loxP synthetic DNA was ligated to SalI digested site of pBRwt. The reaction mixture was doubly digested with restriction enzymes XbaI and XhoI to remove mutant loxP sites which were ligated multiple with both ends of pBRwt, further the unreacted and restriction enzyme digested mutant loxP synthetic DNA were removed from the reaction mixture using GEANCLEAN II (Funakoshi Inc.). The linear DNA (approx. 4.4 kb, FIG. 8), to which a wild-type loxP site in one end and a mutant loxP site in the other end were ligated each other, was obtained. This DNA was used in the following reaction as a substrate DNA.

(2) Cre-dependent Recombination Between Wild-type loxP Site and Mutant loxP Site Reaction and analytical method are the same as in example 1-(4), proviso that the substrate DNA used in this experiment was DNA shown in example 2-(1) in place of DNA shown in example 1-(3).

In the nucleotide sequence of the wild-type loxP site shown hereinbelow (SEQ ID NO: 1, as shown below in both the 5' to 3' and the 3' to 5' direction), it is known that the recombination between two loxP sites is at first initiated with cleavage and religation between bases at position 7 and 8 in the lower DNA strand of the 8-bp spacer region, then terminated by cleavage and re-ligation between bases at position 1 and 2 in the upper DNA strand. (Gue et al. Nature, 389: 40–46, 1997).

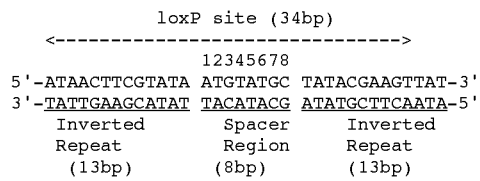

Consequently, in case that the recombination in the lower DNA strand occurs but the recombination in the upper DNA strand does not occur, the result is detected as an intermediate in the reaction. The intermediate was detected as a DNA band close to approx 970 bp in the assay system used by us.

As previously shown in example 1-(4), the DNA band of 920 bp indicates that recombination in both of upper and lower DNA strands completed, and the DNA band of 970 bp indicates the reaction stops in the intermediate.

Table 1 shows the result of analysis, for which existence of these two bands was specifically noticed. Outlines of result in table 1 are shown hereinbelow (numerals after # are SEQ ID NO of mutant loxP site).

11, 12, 13 (SEQ ID NO: 2, 3, 4): reaction proceeded to final stage.

21, 22, 23 (SEQ ID NO: 5, 6, 7): reaction stopped in the intermediate and did not proceed to the final stage.

31, 32, 33 (SEQ ID NO: 8, 9, 10): reaction stopped in the intermediate and did not proceed to the final stage.

41, 42, 43 (SEQ ID NO: 11, 12, 13): reaction stopped in the intermediate and did not proceed to the final stage.

51, 52, 53 (SEQ ID NO: 14, 15, 16): reaction stopped almost in the intermediate and very small portion (about 5%) proceeded to the final stage.

61, 63 (SEQ ID NO: 17, 19): almost no intermediate was produced and very small portion (5–10%) of reaction proceeded to the final stage.

62 (SEQ ID NO: 18): almost no intermediate was produced and a portion (5–10%) of reaction proceeded to the final stage (amount of the final product was more than #61 and 63).

71, 72, 73 (SEQ ID NO: 20, 21, 22): almost no intermediate was produced and very small part of reaction proceeded to the final stage (about 5%, final products was less than #61 and 63).

81, 82, 83 (SEQ ID NO: 23, 24, 25): Reaction proceeded to the final stage.

In conclusion, substitution effect of bases at position from 1 to 8 are summarized according to each substituted position as follows.

(1) The mutant loxP site with substitution at position 1 or 8 reacts with wild type loxP site; (2) The mutant loxP site with substitution at the position 2, 3 or 4 hardly react with wild type loxP site; (3) The mutant loxP site with substitution at position 5, 6 or 7 is difficult to react with wild type loxP site, but react in some part. The above facts become apparent.

These results indicated that substitution of bases at position from 2 to 5 was qualitatively different from the substitution of bases at position 6 and 7, and that in the former, the reaction stopped at the intemrediate stage, and in the latter, the first step of the reaction was markedly inhibited.

Further, according to the result of assay method by us, it has become clear that mutant loxP site (corresponding to #71), which was reported that no specific DNA recombination occurred with wild-type loxP site (Hoess et al., Nucleic Acids Res., 14: 2287–2300, 1986), did not lose reactivity with the wild-type loxP site, and recombination occurs at about 5% of frequency.

EXAMPLE 3

Cre-dependent Recombination Between Wild-type loxP Site and Mutant loxP Site (No. 2)

(1) Preparation of Substrate DNA Containing a Wild-type loxP Site and a Mutant loxP Site Following operations were conducted in order to obtain substrate DNA used for detecting the Cre-dependent recombination between wild-type loxP site and mutant loxP site by more sensitive assay system than the assay system used in examples 1 and 2.

[1] Construction of Plasmid (pBLAmutant) Containing a Wild-type loxP Site and a Mutant loxP Site Following operations were conducted in order to construct plasmid, in which DNA fragment derived from adenovirus type 5 was ligated with a linear DNA fragment of approx. 4.4 kb which was ligated with a wild-type loxP site and a mutant loxP site in both ends of pBR322.

A cosmid vector pAxcw, to which almost full length DNA fragment of adenovirus type 5 except for E1 and E3 genes was inserted (Japanese Patent Unexamined Publication No. Hei 8-308585, page 15), was doubly digested with restriction enzymes XbaI and XhoI. The digested reaction mixture was subjected to agarose gel electrophoresis and a DNA band of approx. 3.8 kb, was excised from the gel, then purified using GEANCLEAN II (Funakoshi Inc.). This DNA fragment of 3.8 kb was ligated with the linear DNA fragment (approx. 4.4 kb as prepared in example 2-(1)-[2]), in which a wild-type loxP site was ligated in one end and a mutant loxP site was ligated in the other end, then E. coli was transformed to obtain plasmid pBLAmutant (8.2 kb, FIG. 9). The plasmid pBLAmutant is a general term of plasmid treated by the above operation. Actually, plasmids having one of mutant loxP site corresponding to #11, #21, #22, #23, #31, #41, #51, #61, #71, #71, #73 or #180 in table 1 and a wild-type loxP site were constructed.

[2] Preparation of Substrate DNA Containing a Wild-type loxP Site and a Mutant loxP Site Following operations were conducted in order to prepare linear DNA fragment containing a wild-type loxP site and a mutant loxP site from plasmid pBLA-mutant used for substrate for Cre-dependent recombination.

Plasmid pBLAmutant, in which an unique restriction enzyme NcoI site was located in the region of inserted adenovirus genome, was digested with restriction enzyme NcoI to prepare linear DNA fragment. The digested reaction mixture was subjected to agarose gel electrophoresis, and a DNA band of approx. 8.2 kb was excised from the gel and purified using GEANCLEAN II (Funakoshi Inc.). This linear DNA of 8.2 kb, was used as substrate in the following reaction.

(2) Cre-dependent Recombination Between a Wild-type loxP Site and a Mutant loxP Site To examine the efficiency of recombination mediated by Cre, the above described substrate DNA and the reaction mixture shown in example 1-(4), were incubated at 37° C. for 30 minutes. After completion of the reaction, 45 µl of TE buffer (pH 8.0) and 5 µl of EDTA solution (pH 8.0) were added to the reaction mixture, extracted with phenol/chloroform and with chloroform, followed ethanol precipitation. The recovered DNA was dissolved in 30 µl of TE buffer (pH 8.0) containing RNase A (20 µg/ml). Half volume thereof was digested with restriction enzyme DraI. The product was subjected to agarose gel electrophoresis, stained with ethidium bromide (EtBr), and detected DNA bands were analyzed.

Figure 10:
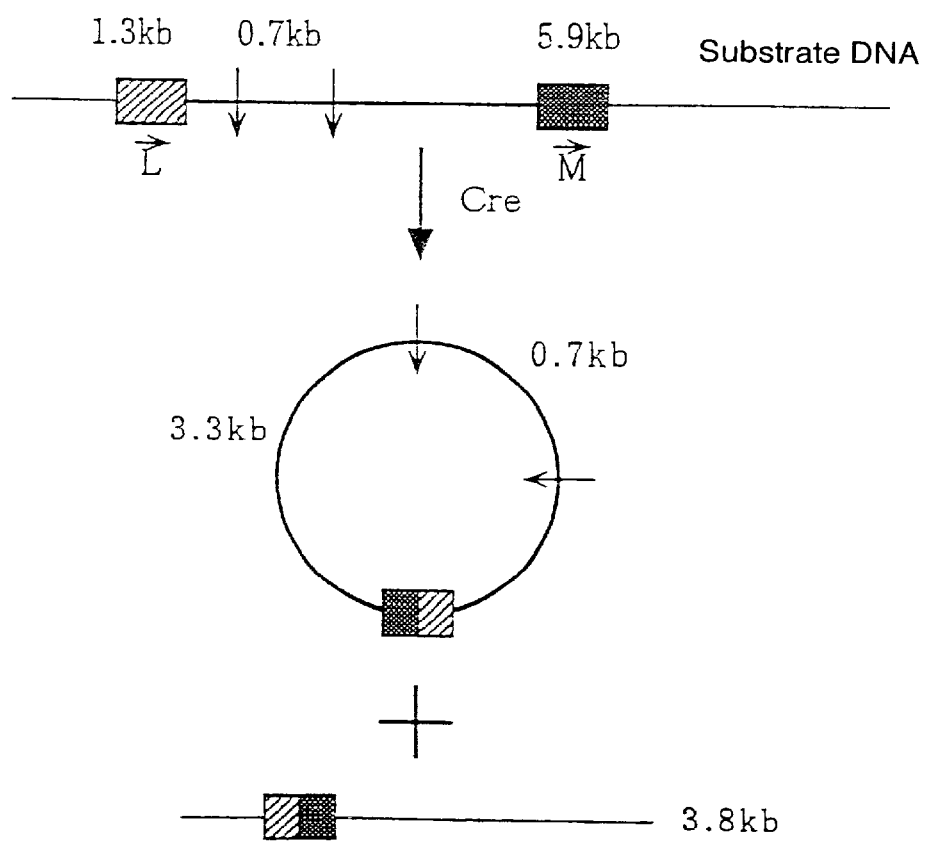
FIG. 10: A schematic drawing showing recombinase Cre dependent recombination between wild-type loxP site and mutant loxP site using linear DNA as substrate. Thin arrow: DraI site.

In the linear DNA fragment used for substrate, since two DraI sites are located between wild-type loxP site and mutant loxP site, in case that recombination mediateed by Cre does not occur, three bands, 5.9 kb, 1.3 kb and 0.7 kb, are generated by DraI digestion (FIG. 10). Contrary to that, as a results of recombination of substrate DNA mediated by Cre, circular DNA of approx. 4 kb containing two DraI sites and one loxP site, and linear DNA fragment of approx. 3.8 kb containing one loxP site and no DraI site, are generated. Digestion of these DNA with DraI generates three bands of 3.8 kb, 3.3 kb and 0.7 kb. Consequently, existence of bands of 3.8 kb and 3.3 kb indicates that recombination mediated by Cre has occurred, and existence of bands of 5.9 kb and 1.3 kb indicates that recombination mediated by Cre has not occurred, and the ratio of the density of these bands indicates efficiency of recombination reaction. Further, the reaction intermediate explained in example 2-(2) was detected as a DNA band of several tens kb in the present assay. Results are summarized as follows.

11, 81: reaction proceeded to the final stage;

21, 22, 23, 31, 41: reaction stopped in the intermediate and did not proceed to the final stage;

51: reaction stopped almost in the intermediate, but very small portion of reaction proceeded to the final stage;

61: almost no intermediate was produced, but some portion of reaction proceeded to the final stage;

71: almost no intermediate was produced, but some portion of reaction proceeded to the final stage (amount of final product was more than #72, 73); and

72, 73: almost no intermediate was produced, but very small portion of reaction proceeded to the final stage.

According to the above results, it was found that the tendency of the reaction was same, even more sensitive assay method than in example 2 was used. Further, even in the mutant loxP site (corresponding to #71), which was reported that no specific DNA recombination occurred with the wild-type loxP site (Hoess et al., Nucleic Acids Res., 14: 2287–2300, 1986), reactivity with the wild-type loxP site was still retained in some part. Furthermore, the level of reactivity of #71 (amount of final product) was higher than that of #72 and #73, which were substituted at the same position, and it was reconfirmed that the substitution in #71 was insufficient to lose the reactivity with wild-type loxP site.

EXAMPLE 4

Cre-dependent Recombination Between Mutant loxP Site with Double-base Substitutions, and Wild-type loxP Site (1) Cre-dependent Recombination Between Wild-type loxP Site and Mutant loxP Site

[1] Preparation of Substrate DNA Containing a Wild-type loxP Site and a Mutant loxP Site Substrate DNA having wild-type loxP site in one end and mutant loxP site in the other end in the linear DNA fragment was prepared according to the method shown in example 2-(1)-[2]. Plasmid pBRwt is a plasmid, to which wild-type loxP site was inserted in plasmid pBR322 (described in example 2-(1)-[1]). pBRwt was digested with SalI and ligated with each mutant loxP site with double-base substitutions (refer to FIG. 4 and FIG. 5). The resulting linear DNA fragments were use as substrate DNA.

[2] Cre-dependent Recombination (No. 1)

According to the melthod as shown in example 1-(4), the efficiency of Cre-dependent recombination was examined using the substrate DNA prepared in [1]. Results are shown in Table 2 (right column).

TABLE 2

Cre-dependent Recombination Reacitons between Wild-type loxP Site and Mutant Type loxP Site (Double-Base Substitutions)

| SEQ ID NO. | Synthetic DNA NO | Mutant loxP Site - Mutant loxP Site | | Wild-type loxP Site - Mutant loxP Site | |
|---|---|---|---|---|---|
| | | Inter-mediate (970 bp) | Final Product (920 bs) | Inter-mediate (970 bp) | Final Product (920 bp) |
| 1 | wild | 1 | 9 | 1 | 9 |
| 20 | #71 | 1 | 6 | 0 | 1 |
| 26 | #2171 | 3 | 3 | 0 | 0 |
| 27 | #2172 | 4 | 2 | | |
| 28 | #2173 | 6 | 0 | | |
| 29 | #2271 | 2 | 6 | | |
| 30 | #2272 | 1 | 6 | 0 | 0 |
| 31 | #2273 | 3 | 4 | | |
| 32 | #2371 | 3 | 2 | | |
| 33 | #2372 | 2 | 0 | | |
| 34 | #2373 | 6 | 1 | 0 | 0 |

TABLE 2-continued

Cre-dependent Recombination Reacitons between Wild-type loxP Site and Mutant Type loxP Site (Double-Base Substitutions)

| SEQ ID NO. | Synthetic DNA NO | Mutant loxP Site - Mutant loxP Site | | Wild-type loxP Site - Mutant loxP Site | |
|---|---|---|---|---|---|
| | | Inter-mediate (970 bp) | Final Product (920 bs) | Inter-mediate (970 bp) | Final Product (920 bp) |
| 35 | #3171 | 4 | 7 | 0 | 0 |
| 36 | #3172 | 0 | 0 | | |
| 37 | #3271 | 3 | 4 | | |
| 38 | #3272 | 6 | 2 | 0 | 0 |
| 39 | #3371 | 5 | 5 | | |
| 40 | #3372 | 6 | 1 | | |
| 41 | #3373 | 6 | 2 | 0 | 0 |
| 42 | #4171 | 0 | 4 | 0 | 0 |
| 43 | #4172 | 2 | 4 | | |
| 44 | #4271 | 4 | 2 | | |
| 45 | #4272 | 4 | 1 | 0 | 0 |
| 46 | #4371 | 4 | 2 | | |
| 47 | #4372 | 3 | 2 | | |
| 48 | #4373 | 7 | 0 | 1 | 0 |
| 49 | #5171 | 0 | 6 | 0 | 0 |
| 50 | #5272 | 1 | 4 | 0 | 0 |
| 51 | #5373 | 1 | 2 | 0 | 0 |
| 52 | #6171 | 0 | 6 | 1 | 1 |
| 53 | #6272 | 1 | 2 | 0 | 0 |
| 54 | #6373 | 1 | 2 | 0 | 0 |

[In the table, amounts of reaction intermediates and final products were indicated in 10 grades with 0–9. Larger number indicated larger amount of production. Amount of final reaction product (density of DNA bands) in case of reaction between two wild-type loxP sites was set as maximum numeral "9", and in case of no DNA band was detected (less than 5% of "9"), the result was set as "0". As for details of reaction intermediates, refer to explanation in example 2-(2).]

In case that mutant loxP site of #6171 was used, the final product (920 bp) was confirmed partially. This result showed that recombination with the wild-type loxP site occurred. However, other mutant loxP sites analyzed, did not react entirely with wild-type loxP site, and the reactivity was lower than the case of mutant loxP site with single-base substitution.

[3] Construction of Plasmid Containing Wild-type loxP Site and Mutant loxP Site

Three types of plasmid pBLAmutant (8.2 kb, refer to FIG. 9) containing both wild-type loxP site and mutant loxP site were constructed from mutant loxP synthetic DNA of #2171, #2272 and #2373, according to a method shown in examples 2-(1)-[2] and 3-(1)-[1].

[4] Cre-dependent Recombination (No. 2.)

After the plasmid constructed in [3] was digested with NheI, linear substrate DNA fragments (8.2 kb) containing wild-type loxP site and mutant loxP site were prepared according to the method shown in example 3-(1)-[2]. According to the method show in example 3-(2), the efficiencies of Cre-dependent recombination were examined using these substrate DNAs. As a result, in all three types of mutant loxP site, both the reaction intermediates and the final products were not produced. Namely, it was shown that mutant loxP site with double-base substitutions did not almost recombine with wild-type loxP site, and it was indicated that the reaction specificity was further increased as compared with a case of mutant loxP site with single-base substitution.

(2) Cre-dependent Recombination Between Two Identical Mutant loxP Stes

[1] Preparation of Substrate DNA Containing Two Mutant loxP Sites

In 29 types of mutant loxP sites (refer to FIG. 4 and FIG. 5), substrate DNAs containing identical mutant loxP site on both ends of linear DNA fragment were prepared according to the method shown in example 1-(3). The above mutant loxP synthetic DNAs were ligated with plasmid pBR322 which was doubly digested with restriction enzymes NheI and SalI, and linear DNA fragments of approx. 4.1 kb, to which identical mutant loxP synthetic DNA were ligated to both ends of pBR322 DNA, were prepared.

[2] Cre-dependent Recombination (No. 1)

According to the method shown in exmaple 1-(4), the efficiencies of Cre-dependent recombination were examined using the substrate DNAs prepared in [1]. Results are shown in Table 2 (left column). Though there were mutant loxP site, which did not occur recombination as like #2173 and #2372, it was confirmed that the recombination occurs in #2271, #2272, #3171, #3371, #4171, #5171 and #6171 with almost same efficiency as in the mutant loxP site with single-base substitution, and in #2171, #2273, #3271 and #4172, about half level of the efficiency in the mutant loxP site with single-base substitution.

[3] Construction of Plasmid Containing One Mutant loxP Site

Figure 7:
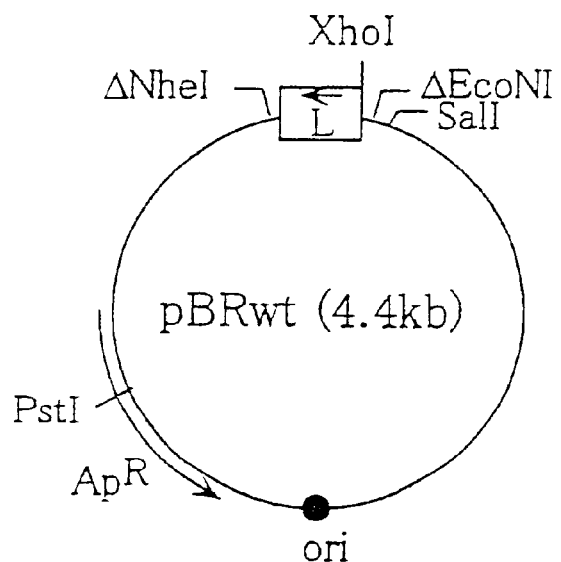
FIG. 7: A schematic drawing showing a structure of plasmid pBRwt. "L": wild-type loxP site. Arrow upper part of letter L: direction for loxP site. ApR: ampicillin resistant gene. ori: replication origin in E. coli.

Using mutant loxP synthetic DNA of #2171, #2272 and #2373, three types of plasmids (pBR2171, pBR2272 and pBR2373, 4.4 kb, respectively, refer to FIG. 7), to which a mutant loxP site was inserted between NheI site and EcoNI site of plasmid pBR322, were constructed according to example 2-(1)-[1].

[4] Construction of Plasmid Containing Two Identical Mutant loxP Sites

Figure 9:
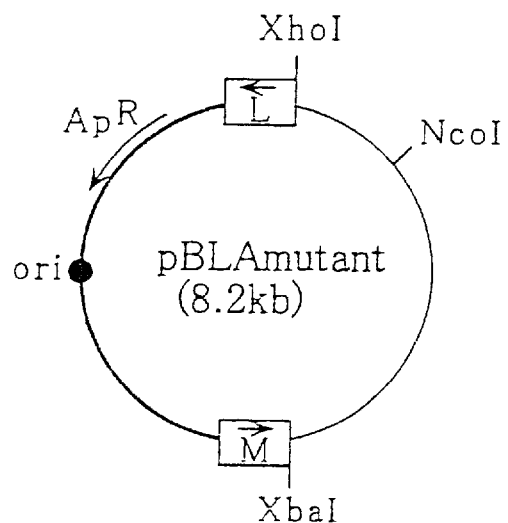
FIG. 9: A schematic drawing showing a structure of plasmid pBLAmutant. Thick line: derived from pBR322. Thin line: derived from adenovirus.

Three types of plasmids (pBR2171, pBR2272 and pBR2373) constructed in [3] were digested with restriction enzyme SalI and ligated with mutant loxP synthetic DNA (#2171, #2272 and #2373) having the same sequence in the plasmid, respectively, then three types of plasmids (pBLA2171x2, pBLA2272x2 and pBLA2373x2, each 8.2 kb, refer to FIG. 9) containing two identical mutant loxP sites were constructed according to methods shown in examples 2-(1)-[2] and 3-(1)-[1].

[5] Cre-dependent Recombination (No. 2)

Three types of plasmids constructed in [4] were digested with restriction enzyme NheI and linear substrate DNA (8.2 kb) containing two identical mutant loxP sites were prepared according to methods shown in example 3-(1)-[2]. According to the method shown in example 3-(2), the efficiencies of Cre-dependent recombination were examioned using these substrate DNAs. As a result, the efficiency of recombination between two mutant loxP sites #2272 was as high as the efficiency of recombination between the wild-type loxP sites. In the mutant loxP site #2171, the reaction proceeded up to final stage, although in some portion reaction stopped in the intermediate. In the mutant loxP site #2373, almost reaction stopped in the intermediate and did not proceed to the final stage.

(3) Examination on Cre-dependent Recombination Between Mutant loxP Sites with Different Sequence

[1] Construction of Plasmid Containing Mutant loxP Sites with Different Sequence Plasmids, pBR2171 and pBR2272 constructed in (2)-[3] were digested with restriction enzyme SalI and ligated with mutant loxP synthetic DNA with different sequence inserted in the plasmid (pBR2171 was ligated with #2272 or #2373 and pBR2272 was ligated with #2373), then three types of plasmids (pBLA2171-2272, pBLA2171-2373 and pBLA2272-2373, each 8.2 kb, refer to FIG. 4) containing two mutant loxP sites with different sequence were constructed according to methods shown in examples 2-(1)-[2] and 3-(1)-[1].

[2] Cre-dependent Recombinant

Plasmids constructed in [1] were digested with restriction enzyme NheI, and the linear substrate DNAs (8.2 kb) containing two mutant loxP sites with different sequence were prepared according to method shown in example 3-(1)-[2]. Using this substrate DNA, the efficiency of Cre-dependent recombination was examined according to the method shown in example 3-(2). As a result, among all combination of three mutant loxP sites with different sequence (#2171, #2272 and #2373), no Cre-dependent recombination occurred. Namely, it was shown that each mutant loxP site could not cross react with other mutant loxP site.

As the results from (1) to (3), it was shown that the recognition specificity of the mutant loxP site with double-base substitutions was higher than that of the mutant loxP site with single-base substituion. Namely, the mutant loxP site with double-base substitutions could not react with neither wild-type loxP site nor mutant loxP site with different sequence. In addition, it was shown that the recombination efficiency between identical mutant loxP sites was as same as the recombination efficiency between wild-type loxP sites. Further, it was shown that the position of substitution was preferably in combination between one of base among base at position 2, 3, 4 and 5 of the spacer region in loxP site and a base at position 7, and even the position of substitution was same, reactivity and reaction specificity are different depending on a kind of base to be substituted. As a result, examples of the mutant loxP site used in the present invention are preferably #2171 (SEQ ID NO: 26), #2271 (SEQ ID NO: 29), #2272 (SEQ ID NO: 30), #3171 (SEQ ID NO: 35), #3371 (SEQ ID NO: 39), #4171 (SEQ ID NO: 42), and #5171 (SEQ ID NO: 49).

EXAMPLE 5

Construction of Plasmid and Cosmid Vector Required for Replacement of Gene Inserted Between Wild-type loxP Site and Mutant loxP Site (1) Construction of Plasmid and Cosmid Vector for Target in Gene Replacement

Figure 11:
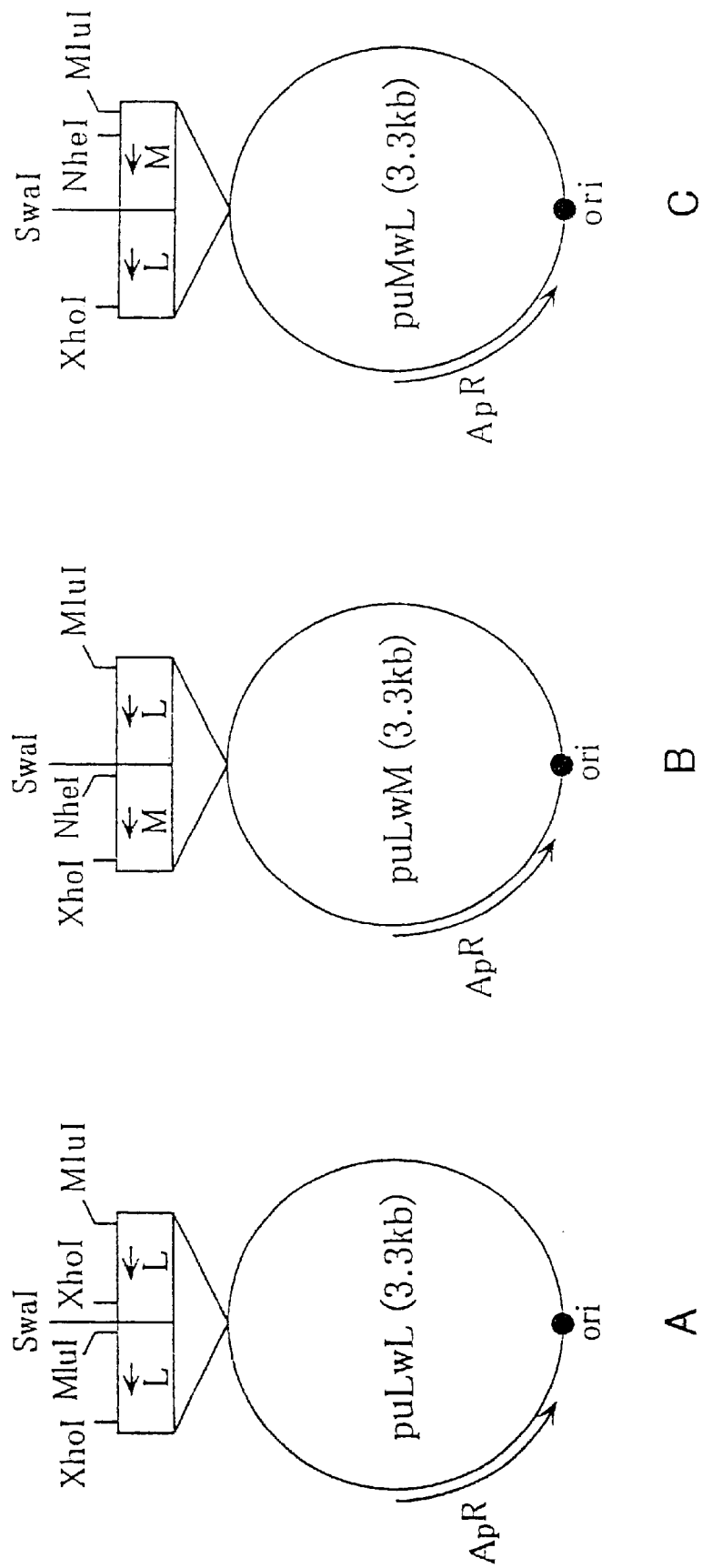
FIG. 11: A schematic drawing showing plasmid puLwL (A), plasmid puLwM (B) and plasmid puMwL (C).

[1] Construction of Plasmid (puLwL) Having Cloning Site Between Two Wild-type loxP Sites Plasmid puLL is a plasmid in which two wild-type loxP sites are inserted with the same direction into the restriction enzyme Ecl136II site of plasmid pUC119 (Kanegae et al., Nucleic Acids Res., 23: 3816–3821, 1995). Following operations were conducted, in order to replace the cloning site between two loxP sites from restriction enzyme NruI site to SwaI site in plasmid puLL.

puLL was digested with restriction enzyme NruI, and ligated with SwaI linker (5'-pGATTTAAATC-3', SEQ ID NO: 61), then again digested with NruI. Repeated digestion of NruI was performed for removing plasmid, in which NruI site was regenerated without ligating SwaI linker. After transformation of E. coli with the reaction mixture, plasmid puLwL (3.3 kb, A in FIG. 11) having SwaI site as a cloning site between two wild-type loxP sites was obtained.

[2] Construction of Plasmid (puLwM and puMwL) Having Cloning Site (SwaI site) Between Wild-type loxP Site and Mutant loxP Site Following operations (A) and (B) were performed in order to construct two types of plasmids, in which one of two wild-type loxP sites in plasmid puLwL was replaced by mutant loxP site. Plasmid puLwM (B in FIG. 11) is a plasmid, in which wild-type loxP site in the left side of puLwL shown in the same figure is replaced by mutant loxP site, and plasmid puMwL (C in FIG. 11) is a plasmid, in which wild-type loxP site in the right side is replaced by mutant loxP site. In this experiment, as for example of mutant loxP site, a mutant sequence of #2171 (SEQ ID NO: 26), in which bases at position 2 and 7 in the spacer region of wild-type loxP site were simultaneously mutated, was used. Mutant loxP site in the following examples is the same as this sequence.

Figure 12:
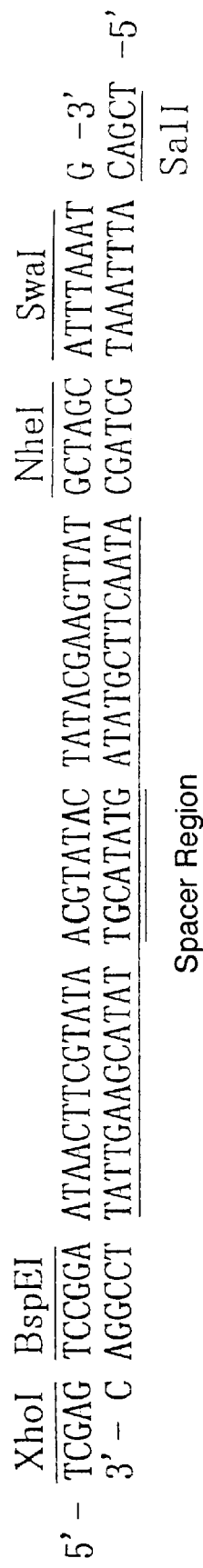
FIG. 12: A nucleotide sequence of mutant type synthetic DNA used for construction of plasmid puLwM (top line of sequence: SEQ ID NO: 57; bottom line of sequence: SEQ ID NO: 58). Underlined part: loxP site. Doubly underlined part: spacer region (8 bp). Thick letter: base substituted.

(A) Construction of puLwM puLwL was digested with restriction enzyme XhoI, and ligated with synthetic DNA of 60 bp, containing mutant loxP site (FIG. 12, upper strand, SEQ ID NO: 57 and lower strand SEQ ID NO: 58), after transformation of E. coli, plasmid puLwM (3.3 kb) bearing SwaI site between wild-type loxP site and mutant loxP site was obtained. Further nucleotide sequence of synthetic DNA part in plasmid puLwM was determined to confirm that wild-type loxP site and mutant loxP site were inserted as intended. Since synthetic DNA used was designed to have the XhoI digested fragment in one end and SalI digested fragment in the other end, XhoI site in the wild-type loxP site of the plasmid puLwM was deleted.

Figure 13:
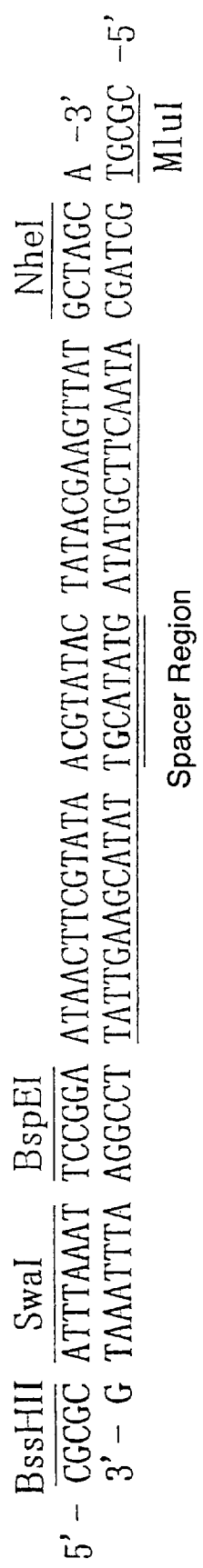
FIG. 13: A nucleotide sequence of mutant type synthetic DNA used for construction of plasmid puMwL (top line of sequence: SEQ ID NO: 59; bottom line of sequence: SEQ ID NO: 60). Underlined part: loxP site. Doubly underlined part: spacer region (8 bp). Thick letter: base substituted.

(B) Construction of puMwL puLwL was digested with restriction enzyme MluI, and ligated with synthetic DNA of 60 bp containing mutant loxP site (FIG. 13, upper strand SEQ ID NO: 59 and lower strand SEQ ID NO: 60), after transformation of E. coli, plasmid puMwL (3.3 kb) bearing SwaI site between wild-type loxP site and mutant loxP site was obtained. Further, as same as the case of the plasmid puLwM, nucleotide sequence in the synthetic DNA part was determined and confirmed the exact insertion. Since synthetic DNA used was designed to have the MluI digested fragment in one end and BssHII digestied fragment in the other end, MluI site in the wild-type loxP site of the plasmid puMwL was deleted.

[3] Construction of Plasmid (PCALL) Inserted with Two Wild-type loxP Sites into the Cloning Site of the CAG Promoter Following DNA were prepared in order to obtain plasmid, to which two wild-type loxP sites were inserted between the promoter and poly(A) sequence in CAG promoter. The CAG promoter herein is disclosed in Japanese Patent Unexamined Publication No. Hei 3-168087 as a high expression vector.

(a) Plasmid pCAGw (Japanese Patent Unexamined Publication No. Hei 8-84589, page 10), in which cloning site of plasmid pCAGGS (Niwa et al., Gene, 108: 193–200, 1991) containing CAG promoter was replaced from EcoRI site to SwaI site, was digested with restriction enzyme SwaI to obtain a linear DNA fragment.

(b) Plasmid puLL (described in [1]) was doubly digested with BamHI and EcoRI, and both ends were blunted with Klenow enzyme, then subjected to agarose gel electrophoresis to obtain DNA fragment of approx. 100 bp, containing two wild-type loxP sites.

DNA fragments of both (a) and (b) were ligated, and the ligation mixture was digested with restriction enzyme SwaI, then E. coli was transformed to obtain plasmid pCALL (4.9 kb).

[4] Construction of Plasmid (pCALwL), in which Cloning Site of Plasmid pCALL was Replaced by SwaI Site Following operation was performed in order to replace the cloning site between two loxP sites in plasmid pCALL from restriction enzyme NruI site to SwaI site.

pCALL was digested with restriction enzyme NruI, and ligated with SwaI linker (5'-pGATTTAAATC-3', SEQ ID NO: 61), and again digested with restriction enzyme NruI. Reason for repeated digestion with NruI is same as in [1]. *E. coli* was transformed by reaction mixture to obtain plasmid pCALwL (4.9 kb, D in FIG. 14) having SwaI site as a cloning site between two wild-type loxP sites in the CAG promoter.

[5] Construction of Plasmid (pCALwM) Inserting Wild-type loxP Site and Mutant loxP Site into the CAG Promoter Following operations were performed in order to obtain plasmid, in which one of wild-type loxP sites in plasmid pCALwL is replaced by mutant loxP site.

(a) Plasmid pCALwL was doubly digested with restriction enzymes MluI and XhoI, and DNA fragment of approx. 4.8 kb without containing wild-type loxP site was recovered after agarose gel electrophoresis.

(b) Plasmid puLwM was doubly digested with restriction enzymes MluI and XhoI, and DNA fragment of 100 kb containing both wild-type loxP site and mutant loxP site was recovered after agarose gel electro-phoresis.

After ligation of both DNA fragments prepared in (a) and (b), *E. coli* was transformed to obtain plasmid pCALwM (4.9 kb, E in FIG. 14). pCALwM is a plasmid having structural component of promoter/wild-type loxP site/SwaI site (cloning site)/mutant loxP site/poly(A) sequence.

[6] Construction of Cosmid Vector (pAxCALwM) for Generation of Recombinant Adenovirus Following operations were performed in order to construct cosmid vector, to which a part from promoter to poly(A) sequence in plasmid pCALwM prepared in [5] was inserted. Construction of cosmid vector was conducted according to known methods (Miyake et al. Proc. Natl. Acad. Sci., 93: 1320–1324, 1996 and Japanese Patent Unexamined Publication No. Hei 7-298877).

(a) Cassette cosmid pAxcw (Japanese Patent Unexamined Publication No. Hei 8-308585, page 15), to which almost full length of adenovirus type 5 DNA except for E1 and E3 gene was inserted, was digested with restriction enzyme SwaI.

(b) Plasmid pCALwM was simultaneously digested with restriction enzymes ApaLI, HindII and HincII, then both ends were blunted with Klenow enzyme, and the reaction mixture was subjected to the agarose gel electro-phoresis to recover the DNA fragment of approx. 2.4 kb.

After ligation of both DNA fragments prepared in (a) and (b), an aliquot of reaction mixture was packaged using lambda in vitro packaging kit (Gigapack XL, Stratagene Corp.), and the reaction mixture was infected to *E. coli*, then cassette cosmid pAxCALwM (44.9 kb) was obtained.

(2) Construction of Plasmid for Target in Gene Replacement

[1] Construction of Plasmid (puLZM) Inserting lacZ Gene Between Wild-type loxP Site and Mutant loxP Site Following operations were conducted in order to obtain plasmid inserting *E. coli* lacZ gene between wild-type loxP site and mutant loxP site in plasmid puLwM (described in (1)-[2]).

(a) Plasmid puLwM was digested with restriction enzyme SwaI, and linear DNA fragment was recovered after agarose gel electrophoresis.

(b) Plasmid pSRlacZ (Miyake et al., Proc. Natl. Acad. Sci., 93: 1320–1324, 1996) was doubly digested with restriction enzyme SalI and PstI, and the both ends were blunted with Klenow enzyme, DNA fragment of approx. 3.1 kb containing lacZ gene was recovered after agarose gel electrophoresis.

After ligation of both DNA fragments prepared in (a) and (b) and digestion with restriction enzyme SwaI, *E. coli* was transformed, and then plasmid puLZM (6.4 kb, F in FIG. 15) was obtained.

[2] Construction of Plasmid (puMOL) Inserting Replication Origin (ori) and poly(A) Sequence of SV40 Between Wild-type loxP Site and Mutant loxP Site Following operation were conducted in order to obtain plasmid which was inserted replication origin (ori) and poly(A) sequence of SV40 between wild type loxP site and mutant loxP site in plasmid puMwL.

(a) Plasmid puMwL (described in (1)-[2]) was digested with restriction enzyme SwaI, and linear DNA fragment was recovered after agarose gel electrophoresis.

(b) Plasmid pCAGGS (described in (1)-[3]) was digested with restriction enzyme BamHI and both ends were blunteld with Klenow enzyme, and then DNA fragment of approx. 340 bp containing ori and poly(A) sequence of SV40 was recovered after agarose gel electrophoresis.

After ligation of both DNA fragments prepared in (a) and (b) and digestion with restriction enzyme SwaI, and *E. coli* was transformed, and then plasmid puMOL (3.6 kb, G in FIG. 15) was obtained.

[3] Construction of Plasmid (puLZMOL) Inserting Wild-type loxP Site/lacZ Gene/mutant loxP Site/ori and poly(A) Sequence of SV40/Wild-type loxP Site Following operations were conducted in order to delete mutant loxP site from plasmid puLZM and therein to insert the DNA fragment containing mutant loxP site/ori and poly(A) sequence of SV40/wild-type loxP site.

(a) Plasmid puLZM was doubly digested with restriction enzymes NheI and XhoI, and the DNA fragment of approx. 6.4 kb containing wild-type loxP site and lacZ gene was recovered after agarose gel electrophoresis.

(b) Plasmid puMOL was doubly digested with restriction enzymes NheI and XhoI, and the DNA fragment of approx. 440 bp containing mutant loxP site ori and poly(A) sequence of SV40/wild-type loxP site was recovered after agarose gel electrophoresis.

After ligation of both DNA fragments prepared in (a) and (b) and digestion with restriction enzyme SwaI, *E. coli* was transformed, and then plasmid puLZMOL (6.8 kb, H in FIG. 16) was obtained.

[4] Construction of Plasmid (puALZMOL) Inserting poly (A) Sequence of Thymidine Kinase Gene into 5'-upstream Region of lacZ Gene in Plasmid puLZMOL Following operations were conducted in order to construct plasmid, to which poly(A) sequence of thymidine kinase (TK) gene of herpes simplex virus type 1 (HSV-1) is inserted into plasmid puLZMOL.

(a) Following operation was conducted in order to obtain the DNA fragment, in which plasmid puLZMOL was cleaved once at the position of the 5'-upstream site of wild-type loxP site located 5'-upstream region of lacZ gene. puLZMOL was digested with restriction enzyme SmaI and then digested with restriction enzyme KpnI. Linear DNA fragment of approx. 6.8 kb was recovered after agarose gel electrophoresis.

(b) Plasmid pTK is a plasmid, in which BamHI digested fragment of approximately 3.6 kb containing TK gene of HSV-1, was inserted into BamHI site of pBR322 (M. Wigler et al., Cell, 14: 725–731, 1978). Poly(A) sequence of approximately 320 bp in TK gene can be excised by digesting pTK with restriction enzymes SmaI and NcoI. Following operation was conducted in order to convert the ends of excised DNA fragment to SmaI and KpnI sites. Plasmid pTK was digested with restriction enzyme NcoI and both ends were blunted with Klenow enzyme. After ligation with KpnI linker (5'-pGGGTACCC-3'), the reaction mixture was digested with restriction enzyme KpnI and then digested with restriction enzyme SmaI. The DNA fragment of approx. 320 bp containing poly(A) sequence of TK gene was recovered after agarose gel electrophoresis.

After ligation of both DNA fragments prepared in (a) and (b), *E. coli* was transformed, and plasmid puALZMOL (7.1 kb, I in FIG. 16) was obtained. puALZMOL is a plasmid having structural component of poly(A) sequence of TK gene/wild-type loxP site/lacz gene/mutant loxP site/ori and poly(A) sequence of SV40/wild-type loxP site. Reason for insertion of poly(A) sequence of TK gene is not to occur the transcription of lacZ gene from unidentified promoter derived from adenovirus located in the upstream of insertion site, when recombinant adenovirus containing a series of above genes is generated.

[5] Construction of Cosmid Vector (pAxALZMOL) to Generate a Recombinant Adenovirus Following operation was conducted in order to construct cosmid vector, in which genes inserted in plasmid puALZMOL (poly(A) sequence of TK gene/wild-type loxP site/lacZ gene/mutant loxP site ori and poly(A) sequence of SV40/wild-type loxP site) was inserted.

Plasmid puALZMOL was simultaneously digested with restriction enzymes XbaI, XhoI and DraI, and the both ends were blunted with Klenow enzyme, the reaction mixture was subjected to agarose gel electrophoresis, and then the DNA fragment of approx. 4.5 kb was recovered. This DNA fragment and cassette cosmid pAxcw digested with restriction enzyme SwaI (prepared in (1)-[6]) were ligated, and digested with restriction enzyme SwaI, and an aliquot of the reaction mixture was packaged using lambda in vitro packaging kit (Gigapack XL, Stratagene Inc.) and the reaction mixture was infected to *E. coli*, and then cassette cosmid pAxALZMOL (46.7 kb) was obtained.

EXAMPLE 6

Generation of Recombinant Adenoviruses Required for Gene Replacement (1) Generation of the Recombinant Adenovirus (AxCALwM) for Target in Gene Replacement Following operation was conducted in order to generate a recombinant adenovirus, in which promoter/wild-type loxP site/SwaI site (cloning site)/mutant loxP site/poly(A) sequence, was inserted into E1 gene deletion site in a replication-deficient adenovirus vector (deletion of E1 and E3 genes). Generation of recombinant adenovirus was performed according to a known method (Miyake et al., Proc. Natl. Acad. Sci., 93: 1320–1324, 1996 and Japanese Patent Unexamined Publication No. Hei 7-298877).

The viral DNA-terminal protein complex of Ad5dlX having an E3 deletion (I. Saito et al., J. Virol., 54: 711–719, 1985), which is a strain derived from human adenovirus type 5, was digested with restriction enzyme EcoT22I. 293 cells were transfected with the viral DNA-terminal protein complex and cosmid vector pAxCALwM constructed in example 5-(1)-[6] by the calcium phosphate coprecipitation method. After the cloning and the selection of generated recombinant adenuviruses, the desired recombinant adenovirus AxCALwM (FIG. 17) was obtained. This recombinant adenovirus was subcultured and purified from 4th or 5th seed of virus stock with high titer by CsCl density-gradient centrifugation (Y. Kanegae et al., Jpn J. Med. Sci. Biol., 47: 157–166, 1994). The resulting purified adenovirus will be used for future experiments.

(2) Generation of Recombinant Adenovirus (AxALZMOL) for Donor in Gene Replacement Following operation was conducted in order to generate a recombinant adenovirus, in which poly(A) sequence of TK gene/wild-type loxP site/lacZ gene/mutant loxP site ori and poly(A) sequence of SV40/wild-type loxP site, were inserted into E1 gene deletion site in a replication-deficient adenovirus vector (E1 and E3 genes were deleted).

293 cells were transfected with restriction enzyme EcoT22I digested viral DNA—terminal protein complex of Ad5-dlX and cosmid vector pAxALZMOL constructed in example 5-(2)-[5] by the calcium phosphate coprecipitation method, and the desired recombinant adenovirus AxALZMOL (FIG. 17) was obtained by means of the same method as in (1). This recombinant adenovirus was also purified from 4th or 5th seed of virus stock by CsCl density-gradient centrifugation. The resulting purified adenovirus will be used for future experiments.

EXAMPLE 7

Construction of Cell Lines for Use of Replacement of Gene on Chromosome of Cells (1) Construction of a Cell Line for Gene Replacement Expressing Hygromycin B Resistant Gene

Figure 18:
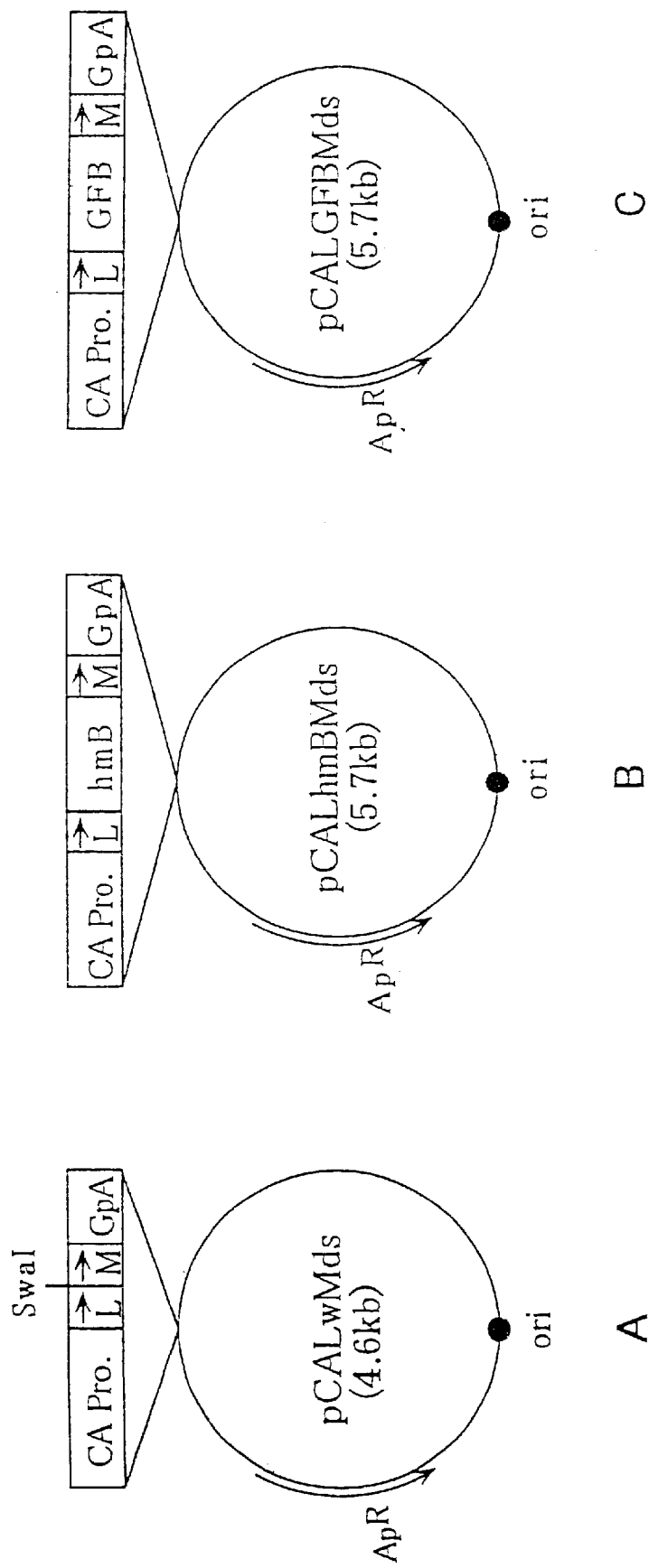
FIG. 18: A schematic drawing showing plasmid pCAL-wMds (A), plasmid pCALhmBMds (B) and plasmid pCAL-GFBMds (C). hmB: hygromycin B resistant gene. GFB: fused gene with GFP and bleomycin resistant gene.

[1] Construction of Plasmid (pCALwMds) for Reporter Gene Insertion Having Cloning Site Between Wild-type loxP Site and Mutant loxP Site Plasmid pCALwM (E in FIG. 14) prepared in example 5-(1)-[5] is a plasmid, in which wild-type loxP site/cloning site (SwaI site)/mutant loxP site is inserted into EcoRI site, a cloning site in the CAG promoter of plasmid pCAGGS (described in example 5-(1)-[3]). Following operation was conducted in order to remove both ori and poly(A) sequence of SV40 from the pCALwM.

pCALwM was digested with BamHI to remove ori and poly(A) sequence of SV40, then after self-ligation, *E. coli* was transformed, and plasmid pCALwMds (4.6 kb, A in FIG. 18) was obtained.

[2] Construction of Plasmid (pCALhmBMds) Inserted with Hygromycin B Resistant Gene Following DNA was prepared in order to construct plasmid, in which hygromycin B resistant gene was inserted into SwaI site of plasmid pCALwMds.

(a) a DNA fragment obtained by digestion of plasmid pCALwMds with restriction enzyme SwaI.

(b) a DNA fragment of approx. 1.1 kb, containing hygromycin B resistant gene, recovered from agarose gel electrophoresis, after doubly digestion of plasmid pCHD2L (Ikeda et al., Gene, 71: 19–27, 1988) with restriction enzymes SmaI and DraI.

After ligation of both DNA fragments of (a) and (b), *E. coli* was transformed, and then plasmid pCALhmBMds (5.7 kb, B in FIG. 18) was obtained. pCALhmBMds is a plasmid, in which hygromycin B resistant gene is inserted between wild-type loxP site and mutant loxP site in the CAG promoter.

[3] Construction of Transformed Cell Line Expressing Hygromycin B Resistant Gene Following operation was conducted in order to obtain transformed cell line having one copy of foreign DNA consisting of promoter/wild-type loxP site/ hygromycin B resistant gene/mutant loxP site/poly(A) sequence on chromosome of cells. Transformation of cells was performed by calcium phosphate DNA coprecipitation method of Chen-Okayama method.

(i) 20 μg of plasmid pCALhmBMds constructed in [2] was dissolved in final concentration of 250 mM calcium chloride solution (volume 100 μl), and 100 μl of 2×BBS solution (50 mM N,N-bis[2-hydroxyethyl]-2-aminoethane sulfonic acid/280 mM NaCl/1.5 mM $Na_2HPO_4$ (pH 6.95) were added. This mixture was added to CV-1 cells cultured in the DMEM medium supplemented with 5% FCS in 6 cm dish, and cultured at 35° C. for about 24 hours in 3% $CO_2$ atmosphere.

(ii) After removal of culture medium, cells were washed with PBS(−), and were added DMEM medium supplemented with 10% FCS, and cultured at 37° C. for overnight in 5% $CO_2$ atmosphere.

(iii) Cells were harvested from 6 cm dish and inoculated to 96 well microplate, further cultured for overnight. Medium containing hygromycin B was added to the cells to final concentration of 0.4 mg/ml, cells were further continued for cultivation, and medium containing hygromycin B was exchanged on 3 to 4 days intervals.

(iv) Survivable cells after about 3 weeks (hygromycin B resistant cell lines) were cloned and expanded, and genomic DNA was extracted from the cell lines. To obtain transformed cell lines, in which only single copy of the objective gene was inserted on a cell chromosome, the genomic DNAs were digested with restriction enzyme PvuII, in which the recognition site was not existed in the plasmid pCALhmB-Mds used for transformation, and digested DNAs were analyzed by Southern blotting using the full length of plasmid pCALhmBMd as a probe. As a result, 18 clones of desired cell lines were obtained. Insertion of single copy of the objective gene was also confirmed by Southern blotting analyzled genomic DNAs of cells digested with restriction enzyme EcoRI, in which only one recognition site exists on plasmid pCALhmBMd.

(2) Construction of Cell Lines for Gene Replacement Expressing Bleomycin Resistant Gene

[1] Construction of Plasmid (pCALGFBMds) Inserted with Bleomycin Resistant Gene

Following operation was conducted in order to construct plasmid inserting bleomycin resistant gene into SwaI site of plasmid pCALwMds.

Plasmid pTracer-CMV (Invitrogene Inc.) was digested with restriction enzyme PmaCI, and subjected to agarose gel electrophoresis, and then a DNA fragment of approx. 1.1 kb containing fusion gene of green fluorescent protein (GFP) and bleomycin resistant gene was recovered. The said DNA fragment was ligated with SwaI digested plasmid pCALw-Mds (prepared in (1)-[2]) and reaction mixture was digested with restriction enzyme SwaI, and *E. coli* was transformed, and then plasmid pCALGFBMds (5.7 kb, C in FIG. 18) was obtained. Plasmid pCALGFBMds is a plasmid, in which gene of fused protein of GFP and bleomycin resistant gene is inserted between wild-type loxP site and mutant loxP site in the CAG promoter.

[2] Construction of Transformed Cell Line Expressing Bleomycin Resistant Gene

Following operation was conducted in order to obtain transformed cell line having single copy of foreign DNA, consisting of promoter/wild-type loxP site/gene of fused protein with GFP and bleomycin resistant gene/mutant loxP site/poly(A) sequence.

Basically, the method is same as in the construction of hygromycin B resistant cell lines shown in (1)-[3]. Only different procedures are explained as follows. Plasmid pCALGFBMds constructed in [2], was used for transformation of CV-1 cells. Bleomycin (final concentration 0.4 mg/ml) was used for drug selection of transformed cells. Full length DNA of pCALGFBMds was used as a probe for Southern blotting for selection of transformants inserted with only single copy of the objective gene.

In order to classify the obtained bleomycin resistant cells (only single copy of objective gene was inserted) with the expression levels of inserted gene, the expression level of GFP was measured. Expression level of GFP was performed by measuring fluorescence at 507 nm by excitation at 478 nm. As a result, cells were classified into: cell lines with high expression of GFP (C18 and C35), cell lines with medium expression (C29 and C38) and cell lines with low expression (C19 and C30)(Numerals show number of cell line).

EXAMPLE 8

Replacement of Gene on Adenovirus Genome

Figure 17:
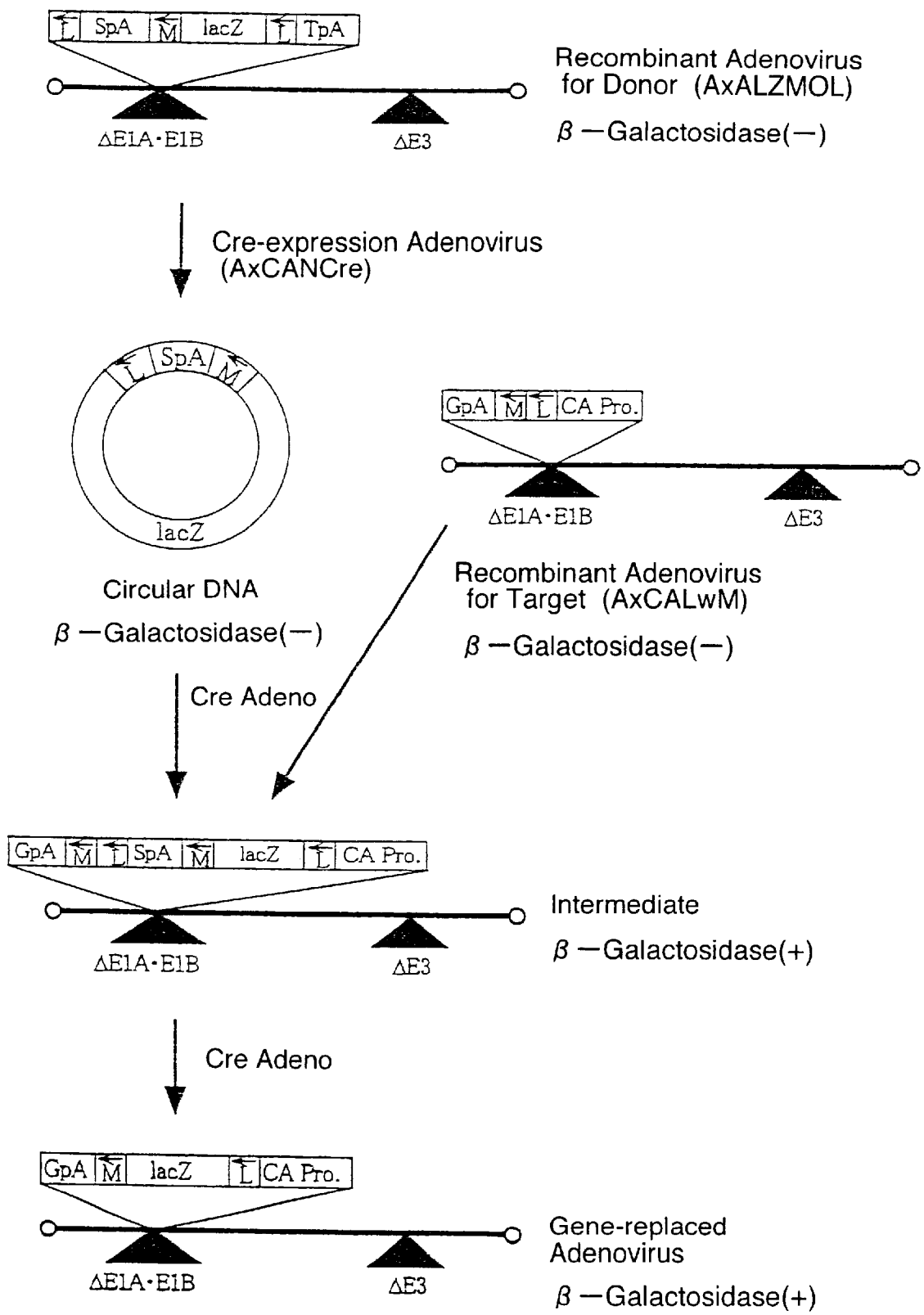
FIG. 17: Schematic drawing for experiment showing that lacZ gene on plasmid DNA (circular DNA) can be inserted onto adenovirus genome by combination of wild-type loxP site and mutant loxP site.

Following experiments were conducted in order to prove that lacZ gene in the plasmid DNA (circular DNA) could be replaced onto adenovirus genome by combination of wild-type loxP site and mutant loxP site. Principle of the experiment is as follows (FIG. 17). Poly(A) sequence of TK gene/wild-type loxP site/lacZ gene/mutant loxP site/ori and poly(A) sequence of SV40/wild-type loxP site are inserted into recombinant adenovirus AXALZMOL for donor generated in example 6. When the cultured cells were doubly infected with this virus and Cre expressing recombinant adenovirus AxCANCre shown in example 1, specific recombination occurred between two wild-type loxP sites, then adenovirus (a) having poly(A) sequence of TK gene/wild-type loxP site and circular DNA (b) having wild-type loxP site/lacZ gene/mutant loxP site ori and poly(A) sequence of SV40 were generated. Since the efficiency of this reaction using recombinant adenovirus inserted with two wild-type loxP sites and Cre expressing recombinant adenovirus is very high (Kanegae et al., Nucleic Acids Res., 23: 3816–3821, 1995), it is expected to generate adenovirus (a) and circular DNA (b) in almost 100% of cultured cells. Though there is a promoter of SV40 ori in the circular DNA (b), lacZ gene can not express, because the transcription of lacZ is blocked by the poly(A) sequence of SV40, which is located adjacently at the downstream of the promoter. When cells, in which the circular DNA (b) was generated, are further infected with recombinant adenovirus AxCALwM for target generated in example 6, recombination between the circular DNA (b) and AxCALwM occurs, then adenovirus (c) having structure of promoter/wild-type loxP site/lacZ gene/mutant loxP sequence/poly(A) sequence is generated through intermediates containing two wild-type loxP sites and two mutant loxP sites. In adenovirus (c), lacZ gene is expressed, and β-galactosidase encoded in lacZ gene is produced, accordingly cells are stained with blue by staining treatment as follows.

Figure 19:
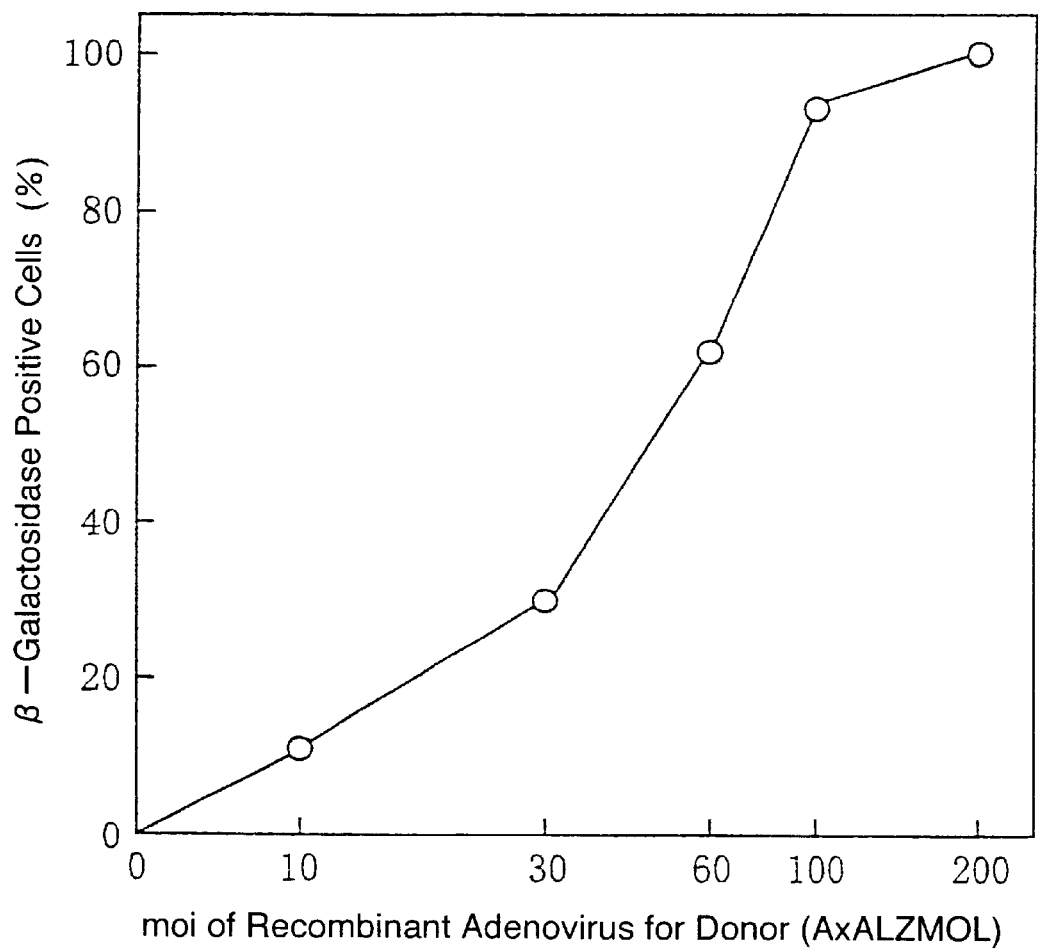
FIG. 19: Result of experiment on gene replacement on adenovirus genome. CV-1 cells were infected with Cre expression recombinant adenovirus at moi 15 and recombinant adenovirus for target at moi 9. Blue stained cells were observed for approximately 60% at moi 60 and approximately 90% at moi 100 of recombinant adenovirus for donor.

In actual experiment, cultured cells (CV-1 cells or COS-1 cells) were simultaneously infected with three types of viruses including recombinant adenovirus AxALZMOL for donor, Cre expressing recombinant adenovirus AxCANCre and recombinant adenovirus AxCALwM for target. Multiplicity of infection (moi) of each virus is as follows. Recombinant adenovirus for target: moi=9, Cre expressing recombinant adenovirus: moi=5 or 15 and recombinant adenovirus for donor: moi=10, 30, 60, 100 and 200. Cells were infected with above viruses for 1 hour, then medium was added and cultured. Three days later, cultured medium was removed and cells were washed with PBS(−) at their surface, and cells were fixed with 0.25% glutaraldehyde solution at 4° C. for 10 minutes, then again washed with PBS(−). X-Gal staining solution [5 mM potassium ferricyanide/5 mM potassium ferrocyanide/2 mM magnesium chloride/1 mg/ml X-Gal (5-bromo-4-chloro-3-indolyl-b-D-galactoside)/PBS(−)] was added and stained for overnight. Results were shown in FIG. 19. FIG. 19 shows result in the case, CV-1 cells were infected with Cre expressing recombinant adenovirus at moi 15. About 60% of cells infected with recombinant adenovirus for donor at moi 60, and about 90% of cells infected at moi 100, were stained. Although not shown in FIG. 19, no blue stained cells were found when cells were infected with only recombinant adenovirus for donor or doubly infected with recombinant adenovirus for donor and Cre expressing recombinant adenovirus. Further, in case that cells were infected with Cre expressing recombinant adenovirus at moi 5, and same experiment using COS-1 cells was conducted, almost same result as in FIG. 19 was obtained.

Above results indicate that, as a result that lacZ gene in genome of recombinant adenovirus for donor was inserted into genome of recombinant adenovirus for target, then lacZ gene was connected directly with promoter and β-galactosidase was expressed, cells were stained with blue. Namely the result clearly proves that lacZ gene between wild-type loxP site and mutant loxP site in the genome of recombinant adenovirus for donor, was replaced with very high efficiency between wild-type loxP site and mutant loxP site in the genome of recombinant adenovirus for target through the form of circular DNA.

EXAMPLE 9
Replacement of Gene on Chromosome of Cells

Figure 20:
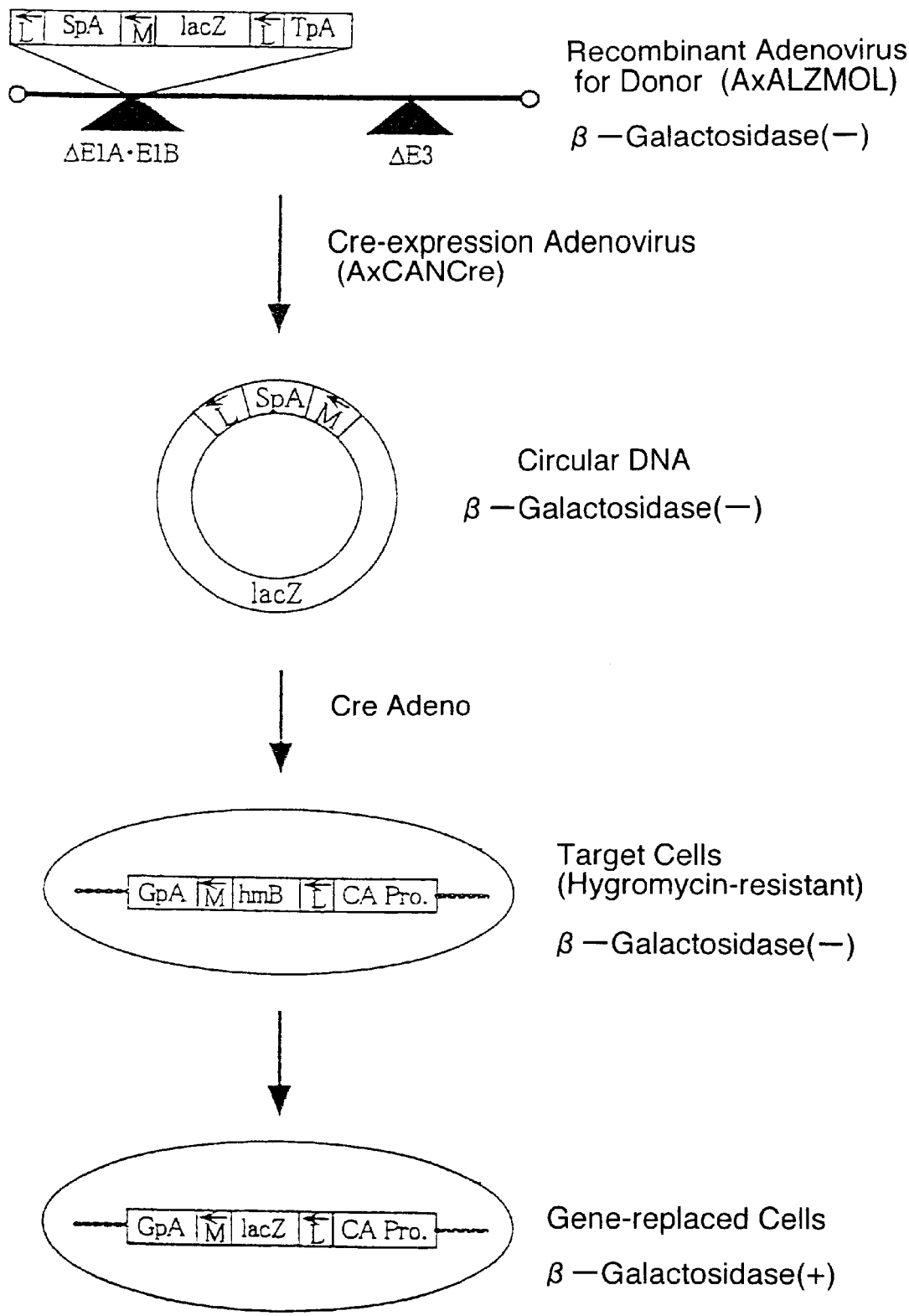
FIG. 20: Schematic drawing for experiment showing that lacZ gene on plasmid DNA (circular DNA) can be integrated onto chromosome of cells by combination of wild-type loxP site and mutant loxP site.

In example 8, it was shown that gene in circular DNA could be replaced into genome of adenovirus. In order to prove that gene can also be replaced into chromosome of cells, following experiment was conducted. The principle is same as in example 8. But instead of recombinant adenovirus for target, transformed cell lines (target cell), constructed in example 7, in which single copy of DNA consisting of promoter/wild-type loxP site/hygromycin B resistant gene/mutant loxP site/poly(A) sequence was inserted into chromosome, was used (FIG. 20).

Figure 21:
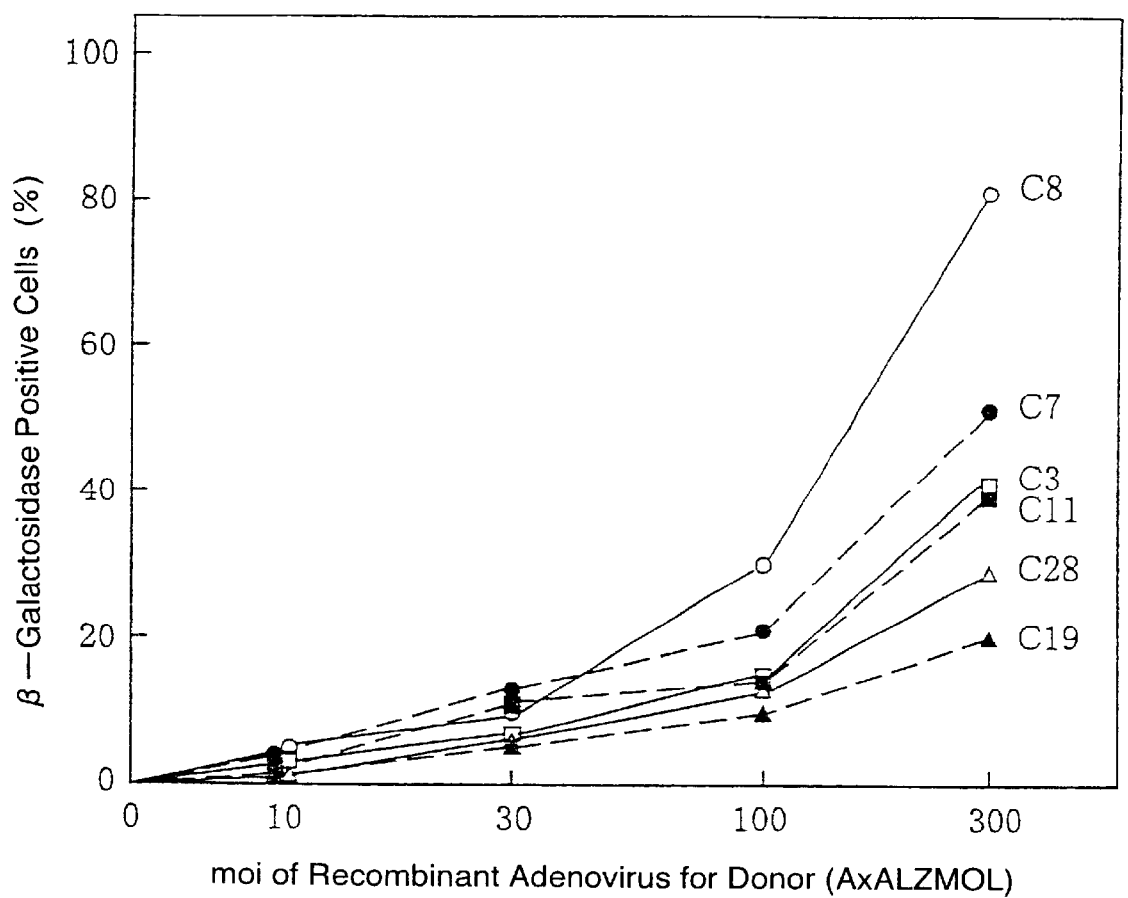
FIG. 21: Result of experiment on gene replacement on chromosome of cells. Six clones of hygromycin resistant target cells (C3, C7, C8, C11, C19 and C28) were infected for 1 hour with Cre expression recombinant adenovirus AxCANCre at moi 5 and recombinant adenovirus for donor AxALZMOL at moi 10, 30, 100 and 300, respectively. Blue stained cells were observed from 10% (C19) to 30% (C8), when cells were infected with recombinant adenovirus for donor at moi 100, although frequency was different as observed depending on cell lines.

Each of any six target cells with hygromycin B resistance constructed in example 7 (C3, C7, C8, C11, C19 and C28) were doubly infected with Cre expressing recombinant adenovirus AxCANCre at moi 5 and recombinant adenovirus for donor AxALZMOL at mois of 10, 30, 100 and 300, respectively, for 1 hour, then medium was added and cultured. Three days later, same operation as shown in example 8 was performed and cells expressed with β-galactosidase were stained. Results are shown in FIG. 21. Although the frequency of expression of β-galactosidase was different depending on cell lines, in case that cells were infected with recombinant adenovirus for donor at moi 100, cells from 10% (C19) to 30% (C8) were stained with blue. When cells were infected with recombinant adenovirus for donor at moi 300, the ratio of cells stained with blue was further increased, however toxicity to cells by large amount of adnovirus particles was observed. Although the data was not shown in figure, in case that cells were infected with only recombinant adenovirus for donor at moi 100 without Cre expressing recombinant adenovirus, there were no cells stained with blue at all.

Above results clearly proved that lacZ gene existed between wild-type loxP site and mutant loxP site in genome of recombinant adenovirus for donor was replaced with high efficiency between wild-type loxP site and mutant loxP site in genome of target cells through formation of circular DNA.

Industrial Applicability

According to the present invention, a mutant loxP site wherein, in the presence of recombinase Cre, recombination with wild-type loxP site can not occur, and recombination between two mutant loxP sites having identical sequence can occur at the almost same efficiency of recombination between two wild-type loxP sites, is provided. Further according to the present invention, a method for gene integration or gene replacement with high efficiency in higher eucaryote including animal cells by the combination of wild-type loxP site and mutant loxP site, or the combination of mutant loxP sites having different sequences in each other, is provided.

Free Text of Sequence Listing

SEQ ID NO: 1: wild-type loxP site;

SEQ ID NO: 2–54: mutant loxP site;

SEQ ID NO: 55: sequence of sense strand designed for containing wild-type loxP site and restriction enzyme recognizing site;

SEQ ID NO: 56: sequence of antisense strand designed for containing wild-type loxP site and restriction enzyme recognizing site;

SEQ ID NO: 57: sequence of sense strand designed for containing mutant loxP site and restriction enzyme recognizing site;

SEQ ID NO: 58: sequence of antisense strand designed for containing mutant loxP site and restriction enzyme recognizing site;

SEQ ID NO: 59: site of sense strand designed for containing mutant loxP site and restriction enzyme recognizing site;

SEQ ID NO: 60: sequence of antisense strand designed for containing mutant loxP site and restriction enzyme recognizing site; and SEQ ID NO: 61: SwI linker.

We claim:

1. A mutant loxP site of a wild-type loxP site derived from E. coli P1 phage represented by SEQ ID NO: 1

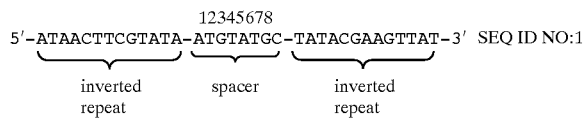

wherein in said mutant loxP site, one nucleotide base in SEQ ID NO: 1 selected from the group consisting of T at position 2 in the spacer, G at position 3 in the spacer, T at position 4 in the spacer, and A at position 5 in the spacer, is substituted by a different nucleotide base; and wherein in said mutant loxP site, one nucleotide base in SEQ ID NO: 1 selected from the group consisting of T at position 6 in the spacer, and G at position 7 in the spacer, is substituted by a different nucleotide base;

wherein, even in the presence of recombinase Cre, said mutant loxP site does not recombine with a wild-type loxP site derived from E. coli P1 phage via a specific DNA recombination event between said mutant loxP site and a wild-type loxP site derived from E. coli P1 phage; and wherein, in the presence of recombinase Cre, said mutant loxP site recombines with a second mutant loxP site which has an identical sequence as said mutant loxP site via a specific DNA recombination event between said mutant loxP site and said second mutant loxP site.

2. The mutant loxP site of claim 1, wherein one or both of said inverted repeats contains at least one nucleotide base substitution.

3. A mutant loxP site of a wild-type loxP site derived from E. coli P1 phage represented by SEQ ID NO: 1

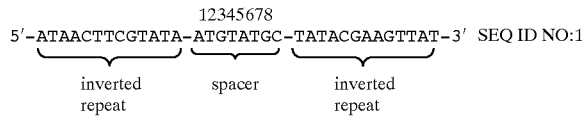

wherein in said mutant loxP site, one nucleotide base in SEQ ID NO: 1 selected from the group consisting of T at position 2 in the spacer, G at position 3 in the spacer, and T at position 4 in the spacer, is substituted by a different nucleotide base;

wherein, even in the presence of recombinase Cre, said mutant loxP site does not recombine with a wild-type loxP site derived from E. coli P1 phage via a specific DNA recombination event between said mutant loxP site and a wild-type loxP site derived from E. coli P1 phage; and wherein, in the presence of recombinase Cre, said mutant loxP site recombines with a second mutant loxP site which has an identical sequence as said mutant loxP site via a specific DNA recombination event between said mutant loxP site and said second mutant loxP site.

4. The mutant loxP site of claim 3, wherein one or both of said inverted repeats contains at least one nucleotide base substitution.

5. The mutant loxP site of claim 1, wherein, in the presence of recombinase Cre, said mutant loxP site does not recombine with a second mutant loxP site which has a different sequence than said mutant loxP site, via a specific DNA recombination event between said mutant loxP site and said second mutant loxP site.

6. The mutant loxP site of claim 3, wherein, in the presence of recombinase Cre, said mutant loxP site does not recombine with a second mutant loxP site which has a different sequence than said mutant loxP site, via a specific DNA recombination event between said mutant loxP site and said second mutant loxP site.

7. The mutant loxP site of claim 1, wherein said mutant loxP site is represented by a member selected from the group consisting of SEQ ID NO: 26, SEQ ID NO: 29, SEQ ID NO: 30, SEQ ID NO: 35, SEQ ID NO: 39, SEQ ID NO: 42, and SEQ ID NO: 49.

8. An isolated DNA molecule comprising the mutant loxP site of any one of claims 1 to 7.

9. An isolated DNA molecule comprising at least one wild-type loxP site derived from E. coli P1 phage and at least one mutant loxP site of claim 1.

10. An isolated DNA molecule comprising at least one wild-type loxP site derived from E. coli P1 phage and at least one mutant loxP site of claim 3.

11. The isolated DNA molecule of claim 9, further comprising a desired DNA molecule inserted between the wild-type loxP site derived from E. coli P1 phage and the mutant loxP site.

12. The isolated DNA molecule of claim 10, further comprising a desired DNA molecule inserted between the wild-type loxP site derived from *E. coli* P1 phage and the mutant loxP site.

13. An isolated DNA molecule comprising at least two mutant loxP sites of claim 5, wherein each mutant loxP site has a different nucleotide sequence.

14. An isolated DNA molecule comprising at least two mutant loxP sites of claim 6, wherein each mutant loxP site has a different nucleotide sequence.

15. The isolated DNA molecule of claim 13, further comprising a desired DNA molecule inserted between the two different mutant loxP sites.

16. The isolated DNA molecule of claim 14, further comprising a desired DNA molecule inserted between the two different mutant loxP sites.

17. A cell which is transformed with the isolated DNA molecule of any one of claims 9 to 16.

18. A method for replacing a desired DNA molecule comprising contacting, in the presence of recombinase Cre, DNA molecule (A) comprising a first desired DNA molecule inserted between a wild-type loxP site derived from *E. coli* P1 phage and a mutant loxP site of claim 1 or 3, with circular DNA molecule (B) comprising a second desired DNA molecule inserted between a wild-type loxP site derived from *E. coli* P1 phage and a mutant loxP site having the same DNA sequence as the mutant loxP site of said DNA molecule (A), so as to cause a recombinational event whereby said first desired DNA molecule in said DNA molecule (A) is replaced by said second desired DNA molecule, wherein said first desired DNA molecule is different from said second desired DNA molecule.

19. A method for replacing a desired DNA molecule comprising contacting, in the presence of recombinase Cre, DNA molecule (A) comprising a first desired DNA molecule inserted between a first mutant loxP site of claim 5 or 6 and a second mutant loxP site of claim 5 or 6, wherein the sequence of said first mutant loxP site is different from the sequence of said second mutant loxP site, with circular DNA molecule (B) comprising a second desired DNA molecule inserted between a mutant loxP site having the same DNA sequence as the first mutant loxP site of said DNA molecule (A) and a second mutant loxP site having the same DNA sequences as the second mutant loxP site of said DNA molecule (A), so as to cause a recombinational event whereby said first desired DNA molecule in said DNA molecule (A) is replaced by said second desired DNA molecule, wherein said first desired DNA molecule is different from said second desired DNA molecule.

20. The method of claim 18, wherein said second desired DNA molecule is not a functional gene.

21. The method of claim 19, wherein said second desired DNA molecule is not a functional gene.

22. The method of claim 18, wherein said first desired DNA molecule is not a functional gene.

23. The method of claim 19, wherein said first desired DNA molecule is not a functional gene.

24. The method of claim 18, wherein said DNA molecule (A) is chromosomal DNA of a cell, and said circular DNA molecule (B) is plasmid DNA or DNA of a double-stranded circular DNA virus.

25. The method of claim 19, wherein said DNA molecule (A) is chromosomal DNA of a cell, and said circular DNA molecule (B) is plasmid DNA or DNA of a double-stranded circular DNA virus.

26. The method of claim 18, wherein said DNA molecule (A) is chromosomal DNA of a cell, and said circular DNA molecule (B) is converted, intracellularly, to double-stranded circular DNA.

27. The method of claim 19, wherein said DNA molecule (A) is chromosomal DNA of a cell, and said circular DNA molecule (B) is converted, intracellularly, to double-stranded circular DNA.

28. The method of claim 18, wherein said DNA molecule (A) is genomic DNA of a double-stranded DNA virus, and said circular DNA molecule (B) is plasmid DNA or DNA of a double-stranded circular DNA virus.

29. The method of claim 19, wherein said DNA molecule (A) is genomic DNA of a double-stranded DNA virus, and said circular DNA molecule (B) is plasmid DNA or DNA of a double-stranded circular DNA virus.

30. The method of claim 18, wherein said DNA molecule (A) is genomic DNA of a double-stranded DNA virus, and said circular DNA molecule (B) is converted, intracellularly, to double-stranded circular DNA.

31. The method of claim 19, wherein said DNA molecule (A) is genomic DNA of a double-stranded DNA virus, and said circular DNA molecule (B) is converted, intracellularly, to double-stranded circular DNA.

32. The method of claim 28, wherein said double-stranded DNA virus is adenovirus.

33. The method of claim 29, wherein said double-stranded DNA virus is adenovirus.

34. A composition comprising the DNA molecule of any one of claims 9 to 16, and a pharmaceutically acceptable carrier or diluent.

* * * * *

SEQUENCE LISTING

<160> NUMBER OF SEQ ID NOS: 61

<210> SEQ ID NO 1
<211> LENGTH: 34
<212> TYPE: DNA
<213> ORGANISM: Bacteriophage P1

<400> SEQUENCE: 1
ataacttcgt ataatgtatg ctatacgaag ttat                      34

<210> SEQ ID NO 2
<211> LENGTH: 34
<212> TYPE: DNA
<213> ORGANISM: Artificial Sequence

```
<220> FEATURE:
<223> OTHER INFORMATION: Sequence of mutant loxP

<400> SEQUENCE: 2
ataacttcgt atagtgtatg ctatacgaag ttat                          34

<210> SEQ ID NO 3
<211> LENGTH: 34
<212> TYPE: DNA
<213> ORGANISM: Artificial Sequence
<220> FEATURE:
<223> OTHER INFORMATION: Sequence of mutant loxP

<400> SEQUENCE: 3
ataacttcgt atattgtatg ctatacgaag ttat                          34

<210> SEQ ID NO 4
<211> LENGTH: 34
<212> TYPE: DNA
<213> ORGANISM: Artificial Sequence
<220> FEATURE:
<223> OTHER INFORMATION: Sequence of mutant loxP

<400> SEQUENCE: 4
ataacttcgt atactgtatg ctatacgaag ttat                          34

<210> SEQ ID NO 5
<211> LENGTH: 34
<212> TYPE: DNA
<213> ORGANISM: Artificial Sequence
<220> FEATURE:
<223> OTHER INFORMATION: Sequence of mutant loxP

<400> SEQUENCE: 5
ataacttcgt ataacgtatg ctatacgaag ttat                          34

<210> SEQ ID NO 6
<211> LENGTH: 34
<212> TYPE: DNA
<213> ORGANISM: Artificial Sequence
<220> FEATURE:
<223> OTHER INFORMATION: Sequence of mutant loxP

<400> SEQUENCE: 6
ataacttcgt ataaagtatg ctatacgaag ttat                          34

<210> SEQ ID NO 7
<211> LENGTH: 34
<212> TYPE: DNA
<213> ORGANISM: Artificial Sequence
<220> FEATURE:
<223> OTHER INFORMATION: Sequence of mutant loxP

<400> SEQUENCE: 7
ataacttcgt ataggtatg ctatacgaag ttat                           34

<210> SEQ ID NO 8
<211> LENGTH: 34
<212> TYPE: DNA
<213> ORGANISM: Artificial Sequence
<220> FEATURE:
<223> OTHER INFORMATION: Sequence of mutant loxP

<400> SEQUENCE: 8
ataacttcgt ataatatatg ctatacgaag ttat                          34
```

```
<210> SEQ ID NO 9
<211> LENGTH: 34
<212> TYPE: DNA
<213> ORGANISM: Artificial Sequence
<220> FEATURE:
<223> OTHER INFORMATION: Sequence of mutant loxP

<400> SEQUENCE: 9
ataacttcgt ataatctatg ctatacgaag ttat                           34

<210> SEQ ID NO 10
<211> LENGTH: 34
<212> TYPE: DNA
<213> ORGANISM: Artificial Sequence
<220> FEATURE:
<223> OTHER INFORMATION: Sequence of mutant loxP

<400> SEQUENCE: 10
ataacttcgt ataatttatg ctatacgaag ttat                           34

<210> SEQ ID NO 11
<211> LENGTH: 34
<212> TYPE: DNA
<213> ORGANISM: Artificial Sequence
<220> FEATURE:
<223> OTHER INFORMATION: Sequence of mutant loxP

<400> SEQUENCE: 11
ataacttcgt ataatgcatg ctatacgaag ttat                           34

<210> SEQ ID NO 12
<211> LENGTH: 34
<212> TYPE: DNA
<213> ORGANISM: Artificial Sequence
<220> FEATURE:
<223> OTHER INFORMATION: Sequence of mutant loxP

<400> SEQUENCE: 12
ataacttcgt ataatgaatg ctatacgaag ttat                           34

<210> SEQ ID NO 13
<211> LENGTH: 34
<212> TYPE: DNA
<213> ORGANISM: Artificial Sequence
<220> FEATURE:
<223> OTHER INFORMATION: Sequence of mutant loxP

<400> SEQUENCE: 13
ataacttcgt ataatggatg ctatacgaag ttat                           34

<210> SEQ ID NO 14
<211> LENGTH: 34
<212> TYPE: DNA
<213> ORGANISM: Artificial Sequence
<220> FEATURE:
<223> OTHER INFORMATION: Sequence of mutant loxP

<400> SEQUENCE: 14
ataacttcgt ataatgtgtg ctatacgaag ttat                           34

<210> SEQ ID NO 15
<211> LENGTH: 34
<212> TYPE: DNA
<213> ORGANISM: Artificial Sequence
<220> FEATURE:
<223> OTHER INFORMATION: Sequence of mutant loxP
```

```
<400> SEQUENCE: 15
ataacttcgt ataatgtttg ctatacgaag ttat                                    34

<210> SEQ ID NO 16
<211> LENGTH: 34
<212> TYPE: DNA
<213> ORGANISM: Artificial Sequence
<220> FEATURE:
<223> OTHER INFORMATION: Sequence of mutant loxP

<400> SEQUENCE: 16
ataacttcgt ataatgtctg ctatacgaag ttat                                    34

<210> SEQ ID NO 17
<211> LENGTH: 34
<212> TYPE: DNA
<213> ORGANISM: Artificial Sequence
<220> FEATURE:
<223> OTHER INFORMATION: Sequence of mutant loxP

<400> SEQUENCE: 17
ataacttcgt ataatgtacg ctatacgaag ttat                                    34

<210> SEQ ID NO 18
<211> LENGTH: 34
<212> TYPE: DNA
<213> ORGANISM: Artificial Sequence
<220> FEATURE:
<223> OTHER INFORMATION: Sequence of mutant loxP

<400> SEQUENCE: 18
ataacttcgt ataatgtaag ctatacgaag ttat                                    34

<210> SEQ ID NO 19
<211> LENGTH: 34
<212> TYPE: DNA
<213> ORGANISM: Artificial Sequence
<220> FEATURE:
<223> OTHER INFORMATION: Sequence of mutant loxP

<400> SEQUENCE: 19
ataacttcgt ataatgtagg ctatacgaag ttat                                    34

<210> SEQ ID NO 20
<211> LENGTH: 34
<212> TYPE: DNA
<213> ORGANISM: Artificial Sequence
<220> FEATURE:
<223> OTHER INFORMATION: Sequence of mutant loxP

<400> SEQUENCE: 20
ataacttcgt ataatgtata ctatacgaag ttat                                    34

<210> SEQ ID NO 21
<211> LENGTH: 34
<212> TYPE: DNA
<213> ORGANISM: Artificial Sequence
<220> FEATURE:
<223> OTHER INFORMATION: Sequence of mutant loxP

<400> SEQUENCE: 21
ataacttcgt ataatgtatc ctatacgaag ttat                                    34

<210> SEQ ID NO 22
```

```
<211> LENGTH: 34
<212> TYPE: DNA
<213> ORGANISM: Artificial Sequence
<220> FEATURE:
<223> OTHER INFORMATION: Sequence of mutant loxP

<400> SEQUENCE: 22
ataacttcgt ataatgtatt ctatacgaag ttat                              34

<210> SEQ ID NO 23
<211> LENGTH: 34
<212> TYPE: DNA
<213> ORGANISM: Artificial Sequence
<220> FEATURE:
<223> OTHER INFORMATION: Sequence of mutant loxP

<400> SEQUENCE: 23
ataacttcgt ataatgtatg ttatacgaag ttat                              34

<210> SEQ ID NO 24
<211> LENGTH: 34
<212> TYPE: DNA
<213> ORGANISM: Artificial Sequence
<220> FEATURE:
<223> OTHER INFORMATION: Sequence of mutant loxP

<400> SEQUENCE: 24
ataacttcgt ataatgtatg gtatacgaag ttat                              34

<210> SEQ ID NO 25
<211> LENGTH: 34
<212> TYPE: DNA
<213> ORGANISM: Artificial Sequence
<220> FEATURE:
<223> OTHER INFORMATION: Sequence of mutant loxP

<400> SEQUENCE: 25
ataacttcgt ataatgtatg atatacgaag ttat                              34

<210> SEQ ID NO 26
<211> LENGTH: 34
<212> TYPE: DNA
<213> ORGANISM: Artificial Sequence
<220> FEATURE:
<223> OTHER INFORMATION: Sequence of mutant loxP

<400> SEQUENCE: 26
ataacttcgt ataacgtata ctatacgaag ttat                              34

<210> SEQ ID NO 27
<211> LENGTH: 34
<212> TYPE: DNA
<213> ORGANISM: Artificial Sequence
<220> FEATURE:
<223> OTHER INFORMATION: Sequence of mutant loxP

<400> SEQUENCE: 27
ataacttcgt ataacgtatc ctatacgaag ttat                              34

<210> SEQ ID NO 28
<211> LENGTH: 34
<212> TYPE: DNA
<213> ORGANISM: Artificial Sequence
<220> FEATURE:
<223> OTHER INFORMATION: Sequence of mutant loxP

<400> SEQUENCE: 28
```
ataacttcgt ataacgtatt ctatacgaag ttat                                    34

<210> SEQ ID NO 29
<211> LENGTH: 34
<212> TYPE: DNA
<213> ORGANISM: Artificial Sequence
<220> FEATURE:
<223> OTHER INFORMATION: Sequence of mutant loxP

<400> SEQUENCE: 29
ataacttcgt ataaagtata ctatacgaag ttat                                    34

<210> SEQ ID NO 30
<211> LENGTH: 34
<212> TYPE: DNA
<213> ORGANISM: Artificial Sequence
<220> FEATURE:
<223> OTHER INFORMATION: Sequence of mutant loxP

<400> SEQUENCE: 30
ataacttcgt ataaagtatc ctatacgaag ttat                                    34

<210> SEQ ID NO 31
<211> LENGTH: 34
<212> TYPE: DNA
<213> ORGANISM: Artificial Sequence
<220> FEATURE:
<223> OTHER INFORMATION: Sequence of mutant loxP

<400> SEQUENCE: 31
ataacttcgt ataaagtatt ctatacgaag ttat                                    34

<210> SEQ ID NO 32
<211> LENGTH: 34
<212> TYPE: DNA
<213> ORGANISM: Artificial Sequence
<220> FEATURE:
<223> OTHER INFORMATION: Sequence of mutant loxP

<400> SEQUENCE: 32
ataacttcgt ataaggtata ctatacgaag ttat                                    34

<210> SEQ ID NO 33
<211> LENGTH: 34
<212> TYPE: DNA
<213> ORGANISM: Artificial Sequence
<220> FEATURE:
<223> OTHER INFORMATION: Sequence of mutant loxP

<400> SEQUENCE: 33
ataacttcgt ataaggtatc ctatacgaag ttat                                    34

<210> SEQ ID NO 34
<211> LENGTH: 34
<212> TYPE: DNA
<213> ORGANISM: Artificial Sequence
<220> FEATURE:
<223> OTHER INFORMATION: Sequence of mutant loxP

<400> SEQUENCE: 34
ataacttcgt ataaggtatt ctatacgaag ttat                                    34

<210> SEQ ID NO 35
<211> LENGTH: 34
<212> TYPE: DNA

```
<213> ORGANISM: Artificial Sequence
<220> FEATURE:
<223> OTHER INFORMATION: Sequence of mutant loxP

<400> SEQUENCE: 35
ataacttcgt ataatatata ctatacgaag ttat                                    34

<210> SEQ ID NO 36
<211> LENGTH: 34
<212> TYPE: DNA
<213> ORGANISM: Artificial Sequence
<220> FEATURE:
<223> OTHER INFORMATION: Sequence of mutant loxP

<400> SEQUENCE: 36
ataacttcgt ataatatatc ctatacgaag ttat                                    34

<210> SEQ ID NO 37
<211> LENGTH: 34
<212> TYPE: DNA
<213> ORGANISM: Artificial Sequence
<220> FEATURE:
<223> OTHER INFORMATION: Sequence of mutant loxP

<400> SEQUENCE: 37
ataacttcgt ataatctata ctatacgaag ttat                                    34

<210> SEQ ID NO 38
<211> LENGTH: 34
<212> TYPE: DNA
<213> ORGANISM: Artificial Sequence
<220> FEATURE:
<223> OTHER INFORMATION: Sequence of mutant loxP

<400> SEQUENCE: 38
ataacttcgt ataatctatc ctatacgaag ttat                                    34

<210> SEQ ID NO 39
<211> LENGTH: 34
<212> TYPE: DNA
<213> ORGANISM: Artificial Sequence
<220> FEATURE:
<223> OTHER INFORMATION: Sequence of mutant loxP

<400> SEQUENCE: 39
ataacttcgt ataatttata ctatacgaag ttat                                    34

<210> SEQ ID NO 40
<211> LENGTH: 34
<212> TYPE: DNA
<213> ORGANISM: Artificial Sequence
<220> FEATURE:
<223> OTHER INFORMATION: Sequence of mutant loxP

<400> SEQUENCE: 40
ataacttcgt ataatttatc ctatacgaag ttat                                    34

<210> SEQ ID NO 41
<211> LENGTH: 34
<212> TYPE: DNA
<213> ORGANISM: Artificial Sequence
<220> FEATURE:
<223> OTHER INFORMATION: Sequence of mutant loxP

<400> SEQUENCE: 41
ataacttcgt ataatttatt ctatacgaag ttat                                    34
```

<210> SEQ ID NO 42
<211> LENGTH: 34
<212> TYPE: DNA
<213> ORGANISM: Artificial Sequence
<220> FEATURE:
<223> OTHER INFORMATION: Sequence of mutant loxP

<400> SEQUENCE: 42
ataacttcgt ataatgcata ctatacgaag ttat                         34

<210> SEQ ID NO 43
<211> LENGTH: 34
<212> TYPE: DNA
<213> ORGANISM: Artificial Sequence
<220> FEATURE:
<223> OTHER INFORMATION: Sequence of mutant loxP

<400> SEQUENCE: 43
ataacttcgt ataatgcatc ctatacgaag ttat                         34

<210> SEQ ID NO 44
<211> LENGTH: 34
<212> TYPE: DNA
<213> ORGANISM: Artificial Sequence
<220> FEATURE:
<223> OTHER INFORMATION: Sequence of mutant loxP

<400> SEQUENCE: 44
ataacttcgt ataatgaata ctatacgaag ttat                         34

<210> SEQ ID NO 45
<211> LENGTH: 34
<212> TYPE: DNA
<213> ORGANISM: Artificial Sequence
<220> FEATURE:
<223> OTHER INFORMATION: Sequence of mutant loxP

<400> SEQUENCE: 45
ataacttcgt ataatgaatc ctatacgaag ttat                         34

<210> SEQ ID NO 46
<211> LENGTH: 34
<212> TYPE: DNA
<213> ORGANISM: Artificial Sequence
<220> FEATURE:
<223> OTHER INFORMATION: Sequence of mutant loxP

<400> SEQUENCE: 46
ataacttcgt ataatggata ctatacgaag ttat                         34

<210> SEQ ID NO 47
<211> LENGTH: 34
<212> TYPE: DNA
<213> ORGANISM: Artificial Sequence
<220> FEATURE:
<223> OTHER INFORMATION: Sequence of mutant loxP

<400> SEQUENCE: 47
ataacttcgt ataatggatc ctatacgaag ttat                         34

<210> SEQ ID NO 48
<211> LENGTH: 34
<212> TYPE: DNA
<213> ORGANISM: Artificial Sequence
<220> FEATURE:

<223> OTHER INFORMATION: Sequence of mutant loxP

<400> SEQUENCE: 48
ataacttcgt ataatggatt ctatacgaag ttat      34

<210> SEQ ID NO 49
<211> LENGTH: 34
<212> TYPE: DNA
<213> ORGANISM: Artificial Sequence
<220> FEATURE:
<223> OTHER INFORMATION: Sequence of mutant loxP

<400> SEQUENCE: 49
ataacttcgt ataatgtgta ctatacgaag ttat      34

<210> SEQ ID NO 50
<211> LENGTH: 34
<212> TYPE: DNA
<213> ORGANISM: Artificial Sequence
<220> FEATURE:
<223> OTHER INFORMATION: Sequence of mutant loxP

<400> SEQUENCE: 50
ataacttcgt ataatgtttc ctatacgaag ttat      34

<210> SEQ ID NO 51
<211> LENGTH: 34
<212> TYPE: DNA
<213> ORGANISM: Artificial Sequence
<220> FEATURE:
<223> OTHER INFORMATION: Sequence of mutant loxP

<400> SEQUENCE: 51
ataacttcgt ataatgtctt ctatacgaag ttat      34

<210> SEQ ID NO 52
<211> LENGTH: 34
<212> TYPE: DNA
<213> ORGANISM: Artificial Sequence
<220> FEATURE:
<223> OTHER INFORMATION: Sequence of mutant loxP

<400> SEQUENCE: 52
ataacttcgt ataatgtaca ctatacgaag ttat      34

<210> SEQ ID NO 53
<211> LENGTH: 34
<212> TYPE: DNA
<213> ORGANISM: Artificial Sequence
<220> FEATURE:
<223> OTHER INFORMATION: Sequence of mutant loxP

<400> SEQUENCE: 53
ataacttcgt ataatgtaac ctatacgaag ttat      34

<210> SEQ ID NO 54
<211> LENGTH: 34
<212> TYPE: DNA
<213> ORGANISM: Artificial Sequence
<220> FEATURE:
<223> OTHER INFORMATION: Sequence of mutant loxP

<400> SEQUENCE: 54
ataacttcgt ataatgtagt ctatacgaag ttat      34

<210> SEQ ID NO 55
<211> LENGTH: 52
<212> TYPE: DNA
<213> ORGANISM: Artificial Sequence
<220> FEATURE:
<223> OTHER INFORMATION: Sense strand of designed sequence containing
sequence of wild-type
loxP and restriction enzyme recognition site

<400> SEQUENCE: 55
tcgaggtgca cataacttcg tataatgtat gctatacgaa gttatacgcg tt                52

<210> SEQ ID NO 56
<211> LENGTH: 52
<212> TYPE: DNA
<213> ORGANISM: Artificial Sequence
<220> FEATURE:
<223> OTHER INFORMATION: Antisense strand of designed sequence
containing sequence of wild
-type loxP and restriction enzyme recognition site

<400> SEQUENCE: 56
ctagaacgcg tataacttcg tatagcatac attatacgaa gttatgtgca cc                52

<210> SEQ ID NO 57
<211> LENGTH: 60
<212> TYPE: DNA
<213> ORGANISM: Artificial Sequence
<220> FEATURE:
<223> OTHER INFORMATION: Sense strand of designed sequence containing
sequence of mutant l
oxP and restriction enzyme recognition site

<400> SEQUENCE: 57
tcgagtccgg aataacttcg tataacgtat actatacgaa gttatgctag catttaaatg        60

<210> SEQ ID NO 58
<211> LENGTH: 60
<212> TYPE: DNA
<213> ORGANISM: Artificial Sequence
<220> FEATURE:
<223> OTHER INFORMATION: Antisense strand of designed sequence
containing sequence of muta
nt loxP and restriction enzyme recognition site

<400> SEQUENCE: 58
tcgacattta aatgctagca taacttcgta tagtatacgt tatacgaagt tattccggac        60

<210> SEQ ID NO 59
<211> LENGTH: 60
<212> TYPE: DNA
<213> ORGANISM: Artificial Sequence
<220> FEATURE:
<223> OTHER INFORMATION: Sense strand of designed sequence containing
sequence of mutant l
oxP and restriction enzyme recognition site

<400> SEQUENCE: 59
cgcgcattta aattccggaa taacttcgta taacgtatac tatacgaagt tatgctagca        60

<210> SEQ ID NO 60
<211> LENGTH: 60
<212> TYPE: DNA
<213> ORGANISM: Artificial Sequence
<220> FEATURE:
<223> OTHER INFORMATION: Antisense strand of designed sequence
containing sequence of muta
nt loxP and restriction enzyme recognition site -continued

```
<400> SEQUENCE: 60
cgcgtgctag cataacttcg tatagtatac gttatacgaa gttattccgg aatttaaatg      60

<210> SEQ ID NO 61
<211> LENGTH: 10
<212> TYPE: DNA
<213> ORGANISM: Artificial Sequence
<220> FEATURE:
<223> OTHER INFORMATION: SwaI liner

<400> SEQUENCE: 61
gatttaaatc                                                             10
```